United States Patent
Hsu et al.

(10) Patent No.: US 8,518,871 B2
(45) Date of Patent: Aug. 27, 2013

(54) SKIN PERMEATING AND CELL ENTERING (SPACE) PEPTIDES AND METHODS OF USE THEREOF

(75) Inventors: Tracy Hsu, Newhall, CA (US); Samir M. Mitragotri, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/253,796

(22) Filed: Oct. 5, 2011

(65) Prior Publication Data

US 2012/0128756 A1 May 24, 2012

Related U.S. Application Data

(60) Provisional application No. 61/411,884, filed on Nov. 9, 2010, provisional application No. 61/527,574, filed on Aug. 25, 2011, provisional application No. 61/528,036, filed on Aug. 26, 2011.

(51) Int. Cl.
| | |
|---|---|
| *A61K 38/00* | (2006.01) |
| *A61K 38/12* | (2006.01) |
| *A61K 38/16* | (2006.01) |
| *A61K 38/10* | (2006.01) |
| *A61K 38/08* | (2006.01) |
| *A61K 38/04* | (2006.01) |
| *A61K 39/00* | (2006.01) |
| *A61K 9/127* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 1/00* | (2006.01) |
| *C07K 14/00* | (2006.01) |
| *C12N 5/00* | (2006.01) |
| *C12N 5/02* | (2006.01) |
| *C12N 15/00* | (2006.01) |

(52) U.S. Cl.
USPC ........... 514/1.2; 514/1.1; 514/21.1; 514/21.6; 514/21.5; 514/21.3; 514/21.4; 530/300; 530/317; 530/324; 530/326; 530/327; 530/328; 530/329; 530/350; 424/133.1; 424/450; 435/331; 435/455

(58) Field of Classification Search
None
See application file for complete search history.

(56) References Cited

U.S. PATENT DOCUMENTS

| | | | |
|---|---|---|---|
| 4,224,179 A | 9/1980 | Schneider | |
| 5,077,057 A | 12/1991 | Szoka, Jr. | |
| 6,083,539 A | 7/2000 | Yamada et al. | |
| 6,747,137 B1 * | 6/2004 | Weinstock et al. | 536/23.1 |
| 2009/0070897 A1 | 3/2009 | Goldman et al. | |
| 2009/0186802 A1 | 7/2009 | Alluis et al. | |
| 2009/0233993 A1 * | 9/2009 | Xu et al. | 514/44 R |
| 2010/0272805 A1 * | 10/2010 | Singh et al. | 424/484 |

OTHER PUBLICATIONS

Heitz, et al., "Twenty years of cell-penetrating peptides: from molecular mechanisms to therapeutics," British J. Pharmacology 157:195-206 (2009).*

(Continued)

*Primary Examiner* — Marcela M Cordero Garcia
*Assistant Examiner* — Thea D'Ambrosio
(74) *Attorney, Agent, or Firm* — Michael B. Rubin; Bozicevic, Field & Francis LLP

(57) ABSTRACT

The present disclosure provides peptides and peptide compositions, which facilitate the delivery of an active agent or an active agent carrier wherein the compositions are capable of penetrating the stratum corneum (SC) and/or the cellular membranes of viable cells.

42 Claims, 12 Drawing Sheets

(56) References Cited

OTHER PUBLICATIONS

Wang, et al., "Synthesis of small cyclic peptides containing the disulfide bond," ARKIVOC (xi), pp. 1-7 (2006).*
EMBL Database, Accession No. ACVC01000718, 3 pages (last updated on Oct. 2010).*
EMBL Database, Accession No. BC053084, 3 pages (last updated 2008).*
EMBL Database, Accession No. DS229040, protein id # EBA51946.1, 26 pages (last updated 2007).*
EMBL Database, Accession No. CH408156, protein id # EDK37787.2, 389 pages (last updated 2009).*
EMBL Database, Accession No. CH408158, protein id # EDK39371.2, 242 pages (last updated 2009).*
Hsu et al., "Peptides as Penetration Enhancers for Transdermal Drug Delivery," 2009 AAPS Annual Meeting and Exposition, abstract, 1 page (Nov. 11, 2009).*
Baskin et al. (2007) "Copper-free click chemistry for dynamic in vivo imaging" *PNAS* 104(43):167393-16797.
Bird et al. (1988) "Single-chain antigen-binding proteins" Science, 242(4877):423-426.
Birkenfeld et al. (1990) "Cross-reactivity between the EBNA-1 p107 peptide, collagen, and keratin: implications for the pathogenesis of rheumatoid arthritis" *Clin Immunol Immunopathol* 54(1):14-25.
Casey (2006) "2005 Nobel Prize in Chemistry. Development of the Olefin Metathesis Method in Organic Synthesis" *J. Chem. Edu.* 83(2):192-195.
Chen et al. (2003) "Advances of Olefin Polymerization in Aqueous Solutions" *Progress in Chemistry* 15: 401-408. Abstract Only.
Chen et al. (2006) "Transdermal protein delivery by a coadministered peptide identified via phage display" *Nat Biotechnol* 24(4):455-460.
Deen (1987) "Hindered transport of large molecules in liquid-filled pores" *AIChE Journal* 33(9):1409-1425.
GenBank Accession: AF301620.1, "*Homo sapiens* interleukin 23 p19 subunit mRNA, complete cds" dated Dec. 4, 2000.
GenBank Accession: NM_000572.2 "*Homo sapiens* interleukin 10 (IL10), mRNA" dated Sep. 18, 2011.
GenBank Accession: NM_000594.2 "*Homo sapiens* tumor necrosis factor (TNF), mRNA" dated Oct. 2, 2011.
GenBank Accession: NM_000880.3 "*Homo sapiens* interleukin 7 (IL7), transcript variant 1, mRNA" dated Oct. 2, 2011.
GenBank Accession: NM_001025366.2 "*Homo sapiens* vascular endothelial growth factor a (VEGFA), transcript variant 1, mRNA" dated Sep. 18, 2011.
GenBank Accession: NM_001025367.2 "*Homo sapiens* vascular endothelial growth factor A (VEGFA), transcript variant 3, mRNA" dated Sep. 18, 2011.
GenBank Accession: NM_001025368.2 "*Homo sapiens* vascular endothelial growth factor A (VEGFA), transcript variant 4, mRNA" dated Sep. 18, 2011.
GenBank Accession: NM_001025369.2 "*Homo sapiens* vascular endothelial growth factor A (VEGFA), transcript variant 5, mRNA" dated Sep. 18, 2011.
GenBank Accession: NM_001025370.2 "*Homo sapiens* vascular endothelial growth factor A (VEGFA), transcript variant 6, mRNA" dated Sep. 18, 2011.
GenBank Accession: NM_001033756.2 "*Homo sapiens* vascular endothelial growth factor A (VEGFA), transcript variant 7, mRNA" dated Sep. 18, 2011.
GenBank Accession: NM_001034.3 "*Homo sapiens* ribonucleotide reductase M2 (RRM2), transcript variant 2, mRNA" dated Oct. 2, 2011.
GenBank Accession: NM_001065.3 "*Homo sapiens* tumor necrosis factor receptor superfamily, member 1A (TNFRSF1A), mRNA" dated Oct. 2, 2011.
GenBank Accession: NM_001165931.1 "*Homo sapiens* ribonucleotide reductase M2 (RRM2), transcript variant 1, mRNA" dated Oct. 2, 2011.
GenBank Accession: NM_001171622.1 "*Homo sapiens* vascular endothelial growth factor A (VEGFA), transcript variant 8, mRNA" dated Sep. 18, 2011.
GenBank Accession: NM_001199886.1 "*Homo sapiens* interleukin 7 (IL7), transcript variant 2, mRNA" dated Oct. 2, 2011.
GenBank Accession: NM_001199887.1 "*Homo sapiens* interleukin 7 (IL7), transcript variant 3, mRNA" dated Oct. 2, 2011.
GenBank Accession: NM_001199888.1"*Homo sapiens* interleukin 7 (IL7), transcript variant 4, mRNA" dated Oct. 2, 2011.
GenBank Accession: NM_001206924.1 "*Homo sapiens* CD86 molecule (CD86), transcript variant 4, mRNA" dated Sep. 25, 2011.
GenBank Accession: NM_001206925.1 "*Homo sapiens* CD86 molecule (CD86), transcript variant 5, mRNA" dated Sep. 25, 2011.
GenBank Accession: NM_003183.4 "*Homo sapiens* ADAM metallopeptidase domain 17 (ADAM17), mRNA" dated Sep. 4, 2011.
GenBank Accession: NM_003376.5 "*Homo sapiens* vascular endothelial growth factor A (VEGFA), transcript variant 2, mRNA" dated Sep. 18, 2011.
GenBank Accession: NM_005554.3 "*Homo sapiens* keratin 6A (KRT6A), mRNA" dated Aug. 14, 2011.
GenBank Accession: NM_006889.4 "*Homo sapiens* CD86 molecule (CD86), transcript variant 2, mRNA" dated Sep. 25, 2011.
GenBank Accession: NM_016584.2 "*Homo sapiens* interleukin 23, alpha subunit p19 (IL23A), mRNA" dated Sep. 25, 2011.
GenBank Accession: NM_020525.4 "*Homo sapiens* interleukin 22 (IL22), mRNA" dated Oct. 2, 2011.
GenBank Accession: NM_175862.4 "*Homo sapiens* CD86 molecule (CD86), transcript variant 1, mRNA" dated Sep. 25, 2011.
GenBank Accession: NM_176892.1 "*Homo sapiens* CD86 molecule (CD86), transcript variant 3, mRNA" dated Sep. 25, 2011.
Geusens et al. (2009) "Cutaneous short-interfering RNA therapy" *Expert Opin Drug Deliv* 6(12):1333-1349.
Gribskov & Burgess (1986) "Sigma factors from *E. coli, B. subtilis*, phage SP01, and phage T4 are homologous proteins" *Nucl. Acids Res.* 14(16):6745-6763.
Guy (1998) "Iontophoresis—recent developments" *J Pharm Pharmacol* 50(4):371-374.
Guy (2010) "Transdermal drug delivery" *Handb Exp Pharmacol* (197):399-410.
Howell et al. (2009) "Cytokine modulation of atopic dermatitis filaggrin skin expression" *J Allergy Clin Immunol* 124(3 Suppl 2):R7-R12.
Hsu and Mitragotri (2011) "Delivery of siRNA and other macromolecules into skin and cells using a peptide enhancer" *Proc. Natl. Acad. Sci. U.S.A.*, 108(38):15816-15821.
Hsu and Mitragotri, AAPS Annual Meeting Abstract, Peptides as Penetration Enhancers for Transdermal Delivery, *AAPS Journal* (2009); 11(S2).
Hsu and Mitragotri, Poster presented on Nov. 11, 2009, at the American Association of Pharmaceutical Scientists (AAPS) 2009 annual meeting.
Hunkapiller & Hood (1986) "The growing immunoglobulin gene superfamily" *Nature* 323(6083):15-16.
Huston et al. (1988) "Protein engineering of antibody binding sites: recovery of specific activity in an anti-digoxin single-chain Fv analogue produced in *Escherichia coli*" *Proc. Natl. Acad. Sci. U.S.A.*, 85(16):5879-5883.
International Search Report for PCT Application No. PCT/US2011/054967, dated May 4, 2012.
Kang et al. (2008) "Identification of a peptide sequence that improves transport of macromolecules across the intestinal mucosal barrier targeting goblet cells" *J Biotechnol* 135(2):210-216.
Karande et al. (2004) "Discovery of transdermal penetration enhancers by high-throughput screening" *Nat Biotechnol* 22(2):192-197.
Karande et al. (2005) "Design principles of chemical penetration enhancers for transdermal drug delivery" *Proc Natl Acad Sci U S A* 102(13):4688-4693.
Kigasawa et al. (2010) "Noninvasive delivery of siRNA into the epidermis by iontophoresis using an atopic dermatitis-like model rat" *Int J Pharm* 383(1-2):157-160.
Kim et al. (2007) "Transdermal delivery enhanced by magainin pore-forming peptide" *J Control Release* 122(3):375-383.
Koh & Geller (1995) "Melanoma control in the United States: current status" *Recent Results Cancer Res* 139:215-224.
Lanzavecchia et al. (1987) "The use of hybrid hybridomas to target human cytotoxic T lymphocytes" *Eur. J. Immunol.* 17(1):105-111.

Leung (1995) "Atopic dermatitis: the skin as a window into the pathogenesis of chronic allergic diseases" *J Allergy Clin Immunol* 96(3):302-319.

Lin et al. (2005) "Mechanistic investigation of the staudinger ligation" *J. Am. Chem. Soc.* 127(8):2686-2695.

Loh et al. (2010) "'Click' synthesis of small molecule-peptide conjugates for organelle-specific delivery and inhibition of lysosomal cysteine proteases" *Chem Commun (Camb)* 46(44):8407-9.

Lopes et al. (2005) "Comparative study of the skin penetration of protein transduction domains and a conjugated peptide" *Pharm Res* 22(5):750-757.

Lynn et al. (2000) "Water-Soluble Ruthenium Alkylidenes: Synthesis, Characterization, and Application to Olefin Metathesis in Protic Solvents" *J. Am. Chem. Soc.* 122(28):6601-6609.

Magnusson et al. (2004) "Simple rules defining the potential of compounds for transdermal delivery or toxicity" *Pharm Res* 21(6):1047-1054.

Mayer et al. (1986) "Techniques for encapsulating bioactive agents into liposomes" *Chemistry and Physics of Lipids*, 40(204):333-345.

Mitragotri et al. (1995) "Ultrasound-mediated transdermal protein delivery" *Science* 269(5225):850-853.

Mitragotri (2003) "Modeling skin permeability to hydrophilic and hydrophobic solutes based on four permeation pathways" *J Control Release* 86(1):69-92.

Mitragotri et al. (2011) "Mathematical models of skin permeability: An overview" *Int J Pharm* 418(1):115-129.

Morris et al. (2011) "Enhanced pulmonary absorption of a macromolecule through coupling to a sequence-specific phage display-derived peptide" *J Control Release* 151(1):83-94.

Nakase et al. (2004) "Cellular uptake of arginine-rich peptides: roles for macropinocytosis and actin rearrangement" *Mol Ther* 10(6):1011-1022.

Nichols & Cook-Bolden (2009) "Allergic skin disease: major highlights and recent advances" *Med Clin North Am* 93(6):1211-1224.

Otto (2009) "Staphylococcus epidermidis—the 'accidental' pathogen" *Nat Rev Microbiol* 7(8):555-567.

Palmer et al. (2006) "Common loss-of-function variants of the epidermal barrier protein filaggrin are a major predisposing factor for atopic dermatitis" *Nat Genet* 38(4):441-446.

Patel et al. (2007) "Cell penetrating peptides: intracellular pathways and pharmaceutical perspectives" *Pharm Res* 24(11):1977-1992.

Peck et al. (1994) "Hindered diffusion of polar molecules through and effective pore radii estimates of intact and ethanol treated human epidermal membrane" *Pharm Res* 11(9):1306-1314.

Polat (2010) "Application of the aqueous porous pathway model to quantify the effect of sodium lauryl sulfate on ultrasound-induced skin structural perturbation" *J Pharm Sci* Epub:1-17.

Potts Ro & Guy (1992) "Predicting skin permeability" *Pharm Res* 9(5):663-669.

Prausnitz & Langer (2008) "Transdermal drug delivery" *Nat Biotechnol* 26(11):1261-1268.

Prausnitz (2004) "Microneedles for transdermal drug delivery" *Adv Drug Deliv Rev* 56(5):581-587.

Ritprajak et al. (2008) "Topical application of cream-emulsified CD86 siRNA ameliorates allergic skin disease by targeting cutaneous dendritic cells" *Mol Ther* 16(7):1323-1330.

Rostovtsev et al. (2002) "A stepwise huisgen cycloaddition process: copper(I)-catalyzed regioselective 'ligation' of azides and terminal alkynes" *Angew. Chem. Int. Ed.* 41(14):2596-2599.

Rothbard et al. (2000) "Conjugation of arginine oligomers to cyclosporin A facilitates topical delivery and inhibition of inflammation" *Nat Med* 6(11):1253-1257.

Sawant & Torchilin (2010) "Intracellular transduction using cell-penetrating peptides" *Mol Biosyst* 6(4):628-640.

Saxon & Bertozzi (2000) "Cell surface engineering by a modified Staudinger reaction" Mar. 17 *Science* 287(5460):2007-2010.

Seto et al. (2010) "Effects of ultrasound and sodium lauryl sulfate on the transdermal delivery of hydrophilic permeants: Comparative in vitro studies with full-thickness and split-thickness pig and human skin" *J Control Release* 145(1):26-32.

Tamaru et al. (2010) "Leptin-derived peptide, a targeting ligand for mouse brain-derived endothelial cells via macropinocytosis" *Biochem Biophys Res Commun* 394(3):587-592.

Tang et al. (2001) "Theoretical description of transdermal transport of hydrophilic permeants: application to low-frequency sonophoresis" *J Pharm Sci* 90(5):545-568.

Tang et al. (2002) "Effects of low-frequency ultrasound on the transdermal permeation of mannitol: comparative studies with in vivo and in vitro skin" *J Pharm Sci* 91(81):1776-1794.

Tang et al. (2002) "Prediction of steady-state skin permeabilities of polar and nonpolar permeants across excised pig skin based on measurements of transient diffusion: characterization of hydration effects on the skin porous pathway" *J Pharm Sci* 91(8):1891-1907.

Tezel A & Mitragotri (2003) "On the origin of size-dependent tortuosity for permeation of hydrophilic solutes across the stratum corneum" *J Control Release* 86(1):183-186.

Tezel et al. (2002) "A theoretical analysis of low-frequency sonophoresis: dependence of transdermal transport pathways on frequency and energy density" *Pharm Res* 19(12):1841-1846.

Tezel et al. (2003) "Description of transdermal transport of hydrophilic solutes during low-frequency sonophoresis based on a modified porous pathway model" *J Pharm Sci* 92(2):381-393.

Thompson (2004) "Small-molecule-protein conjugation procedures" *Methods Mol Med*. 94:255-65.

Tornøe et al. (2002) "Peptidotriazoles on solid phase: [1,2,3]-triazoles by regiospecific copper(i)-catalyzed 1,3-dipolar cycloadditions of terminal alkynes to azides" *J. Org. Chem*. 67(9):3057-3064.

Walsh et al. (2006) "Evaluation of cellular uptake and gene transfer efficiency of pegylated poly-L-lysine compacted DNA: implications for cancer gene therapy" *Mol Pharm* 3(6):644-653.

\* cited by examiner

SEQUENCE LISTING

<160> NUMBER OF SEQ ID NOS: 29

<210> SEQ ID NO 1
<211> LENGTH: 7
<212> TYPE: PRT
<213> ORGANISM: Artificial Sequence
<220> FEATURE:
<223> OTHER INFORMATION: identified using phage display

```
<400> SEQUENCE: 1

Thr Gly Ser Thr Gln His Gln
 1               5

<210> SEQ ID NO 2
<211> LENGTH: 7
<212> TYPE: PRT
<213> ORGANISM: Artificial Sequence
<220> FEATURE:
<223> OTHER INFORMATION: identified using phage display

<400> SEQUENCE: 2

His Ser Ala Leu Thr Lys His
 1               5

<210> SEQ ID NO 3
<211> LENGTH: 7
<212> TYPE: PRT
<213> ORGANISM: Artificial Sequence
<220> FEATURE:
<223> OTHER INFORMATION: identified using phage display

<400> SEQUENCE: 3

Lys Thr Gly Ser His Asn Gln
 1               5

<210> SEQ ID NO 4
<211> LENGTH: 7
<212> TYPE: PRT
<213> ORGANISM: Artificial Sequence
<220> FEATURE:
<223> OTHER INFORMATION: identified using phage display

<400> SEQUENCE: 4

Met Gly Pro Ser Ser Met Leu
 1               5

<210> SEQ ID NO 5
<211> LENGTH: 7
<212> TYPE: PRT
<213> ORGANISM: Artificial Sequence
<220> FEATURE:
<223> OTHER INFORMATION: identified using phage display

<400> SEQUENCE: 5

Thr Asp Pro Asn Gln Leu Gln
 1               5

<210> SEQ ID NO 6
<211> LENGTH: 7
<212> TYPE: PRT
<213> ORGANISM: Artificial Sequence
<220> FEATURE:
<223> OTHER INFORMATION: identified using phage display

<400> SEQUENCE: 6

Ser Thr His Phe Ile Asp Thr
 1               5

<210> SEQ ID NO 7
<211> LENGTH: 9
<212> TYPE: PRT
<213> ORGANISM: Artificial Sequence
<220> FEATURE:
<223> OTHER INFORMATION: identified using phage display

<400> SEQUENCE: 7
```

```
Cys Thr Gly Ser Thr Gln His Gln Cys
 1               5

<210> SEQ ID NO 8
<211> LENGTH: 9
<212> TYPE: PRT
<213> ORGANISM: Artificial Sequence
<220> FEATURE:
<223> OTHER INFORMATION: identified using phage display

<400> SEQUENCE: 8

Cys His Ser Ala Leu Thr Lys His Cys
 1               5

<210> SEQ ID NO 9
<211> LENGTH: 9
<212> TYPE: PRT
<213> ORGANISM: Artificial Sequence
<220> FEATURE:
<223> OTHER INFORMATION: identified using phage display

<400> SEQUENCE: 9

Cys Lys Thr Gly Ser His Asn Gln Cys
 1               5

<210> SEQ ID NO 10
<211> LENGTH: 9
<212> TYPE: PRT
<213> ORGANISM: Artificial Sequence
<220> FEATURE:
<223> OTHER INFORMATION: identified using phage display

<400> SEQUENCE: 10

Cys Met Gly Pro Ser Ser Met Leu Cys
 1               5

<210> SEQ ID NO 11
<211> LENGTH: 9
<212> TYPE: PRT
<213> ORGANISM: Artificial Sequence
<220> FEATURE:
<223> OTHER INFORMATION: identified using phage display

<400> SEQUENCE: 11

Cys Thr Asp Pro Asn Gln Leu Gln Cys
 1               5

<210> SEQ ID NO 12
<211> LENGTH: 9
<212> TYPE: PRT
<213> ORGANISM: Artificial Sequence
<220> FEATURE:
<223> OTHER INFORMATION: identified using phage display

<400> SEQUENCE: 12

Cys Ser Thr His Phe Ile Asp Thr Cys
 1               5

<210> SEQ ID NO 13
<211> LENGTH: 11
<212> TYPE: PRT
<213> ORGANISM: Artificial Sequence
<220> FEATURE:
<223> OTHER INFORMATION: identified using phage display

<400> SEQUENCE: 13

Ala Cys Thr Gly Ser Thr Gln His Gln Cys Gly
 1               5                  10
```

```
<210> SEQ ID NO 14
<211> LENGTH: 11
<212> TYPE: PRT
<213> ORGANISM: Artificial Sequence
<220> FEATURE:
<223> OTHER INFORMATION: identified using phage display

<400> SEQUENCE: 14

Ala Cys His Ser Ala Leu Thr Lys His Cys Gly
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: identified using phage display

<400> SEQUENCE: 15

Ala Cys Lys Thr Gly Ser His Asn Gln Cys Gly
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: identified using phage display a

<400> SEQUENCE: 16

Ala Cys Met Gly Pro Ser Ser Met Leu Cys Gly
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: identified using phage display

<400> SEQUENCE: 17

Ala Cys Thr Asp Pro Asn Gln Leu Gln Cys Gly
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: identified using phage display

<400> SEQUENCE: 18

Ala Cys Ser Thr His Phe Ile Asp Thr Cys Gly
 1               5                  10

<210> SEQ ID NO 19
<211> LENGTH: 6
<212> TYPE: DNA
<213> ORGANISM: Artifiicial Sequence
<220> FEATURE:
<223> OTHER INFORMATION: portion of artificial DNA sequence,
      specifically a vector restriction site.

<400> SEQUENCE: 19 cggccg                                                                      6
```

-continued

```
<210> SEQ ID NO 20
<211> LENGTH: 6
<212> TYPE: DNA
<213> ORGANISM: Artificial Sequence
<220> FEATURE:
<223> OTHER INFORMATION: portion of artificial DNA sequence,
      specifically a vector restriction site.

<400> SEQUENCE: 20 ccgcgg                                                                      6

<210> SEQ ID NO 21
<211> LENGTH: 39
<212> TYPE: DNA
<213> ORGANISM: Artificial Sequence
<220> FEATURE:
<223> OTHER INFORMATION: forward primer

<400> SEQUENCE: 21
gttccgcgga aactgttgaa agttgtttag caaaatccc                                 39

<210> SEQ ID NO 22
<211> LENGTH: 7
<212> TYPE: PRT
<213> ORGANISM: Artificial Sequence
<220> FEATURE:
<223> OTHER INFORMATION: portion of a control peptide amino acid
      sequence

<400> SEQUENCE: 22

Thr His Gly Gln Thr Gln Ser
 1               5

<210> SEQ ID NO 23
<211> LENGTH: 102
<212> TYPE: DNA
<213> ORGANISM: Artificial Sequence
<220> FEATURE:
<223> OTHER INFORMATION: reverse primer

<400> SEQUENCE: 23
tttccgcgga acctccaccg cactgatgct gctcgaacca gtacaagcag agtgagaata         60
gaaaggtact actaaaggaa ttgcgaataa taatttttc ac                            102

<210> SEQ ID NO 24
<211> LENGTH: 82
<212> TYPE: DNA
<213> ORGANISM: Artificial Sequence
<220> FEATURE:
<223> OTHER INFORMATION: reverse primer

<400> SEQUENCE: 24
tttccgcgga acctccaccg caacaagcag agtgagaata gaaaggtact actaaaggaa         60
ttgcgaataa taatttttc ac                                                   82

<210> SEQ ID NO 25
<211> LENGTH: 11
<212> TYPE: PRT
<213> ORGANISM: Artificial Sequence
<220> FEATURE:
<223> OTHER INFORMATION: control peptide amino acid sequence

<400> SEQUENCE: 25

Ala Cys Thr His Gly Gln Thr Gln Ser Cys Gly
 1               5                  10
```

```
<210> SEQ ID NO 26
<211> LENGTH: 21
<212> TYPE: RNA
<213> ORGANISM: Artificial Sequence
<220> FEATURE:
<223> OTHER INFORMATION: Green Fluorescent Protein (GFP) siRNA

<400> SEQUENCE: 26
gacguaaacg gccacaaguu c                                              21

<210> SEQ ID NO 27
<211> LENGTH: 21
<212> TYPE: RNA
<213> ORGANISM: Artificial Sequence
<220> FEATURE:
<223> OTHER INFORMATION: Interleukin-10 (IL-10) siRNA sequence

<400> SEQUENCE: 27
gaaugaauuu gacaucuucu u                                              21

<210> SEQ ID NO 28
<211> LENGTH: 21
<212> TYPE: RNA
<213> ORGANISM: Artificial Sequence
<220> FEATURE:
<223> OTHER INFORMATION: luciferase (control) siRNA sequence
      siRNA sequence

<400> SEQUENCE: 28
uaaggcuaug aagagauacu u                                              21

<210> SEQ ID NO 29
<211> LENGTH: 21
<212> TYPE: RNA
<213> ORGANISM: Artificial Sequence
<220> FEATURE:
<223> OTHER INFORMATION: glyceraldehyde 3-phosphate dehydrogenase
      (GAPDH) siRNA sequence

<400> SEQUENCE: 29
gugugaacca cgagaaauau u                                              21
```

US 8,518,871 B2

SKIN PERMEATING AND CELL ENTERING (SPACE) PEPTIDES AND METHODS OF USE THEREOF

CROSS REFERENCE TO RELATED APPLICATIONS

This application claims priority to U.S. Provisional Patent Application No. 61/411,884, filed Nov. 9, 2010, and entitled "Peptides to Facilitate Drug Delivery"; 61/527,574, filed Aug. 25, 2011, and entitled "Skin Permeating and Cell Entering (SPACE) Peptides and Methods of Use Thereof"; and 61/528,036, filed Aug. 26, 2011, and entitled "Skin Permeating and Cell Entering (SPACE) Peptides and Methods of Use Thereof", which applications are incorporated by reference herein in their entireties and for all purposes.

GOVERNMENT RIGHTS

This invention was made with Government support under Federal Grant No. 1UO1 HL080718 awarded by the National Institutes of Health and Federal Grant No. 1S10RR017753-01 awarded by the National Center for Research Resources. The Government has certain rights in this invention.

BACKGROUND

Skin, the largest organ of the human body, is a host to numerous dermatological diseases which collectively represent a large category of human health conditions. Accordingly, successful delivery of therapeutics, e.g., macromolecules such as siRNA, into skin has become a topic of active research and development. The goal of topical siRNA delivery, however, is extremely challenging and with some exceptions, has been very difficult to accomplish. The primary challenge is poor skin penetration of macromolecules. Among various physico-chemical methods proposed to enhance penetration of macromolecules, peptide carriers have emerged as potential candidates owing to their simplicity of use, diversity and potential ability to target cellular sub-types within the skin. Several peptides including TAT, polyarginine, meganin, and penetratin, which were initially identified for delivering drugs into the cytoplasm of cells, have been tested for penetration across the stratum corneum (SC) and a few have shown some efficacy in delivering small molecules into the epidermis. In contrast, only one peptide, TD-1, has been specifically shown to penetrate the SC and possess the ability to enhance systemic uptake of topically applied drugs. Although several peptides are known to penetrate cellular membranes and a few to penetrate the SC, peptides that simultaneously enhance the penetration of macromolecules and other actives across the SC and/or across the cellular membranes of viable epidermal and dermal cells are needed.

SUMMARY OF THE INVENTION

The present disclosure provides peptides and peptide compositions which facilitate the delivery of an active agent or an active agent carrier wherein the compositions are capable of penetrating the SC and/or the cellular membranes of viable cells.

In a first aspect, the present disclosure provides a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is conjugated to an active agent or an active agent carrier including the active agent, and wherein the composition is capable of penetrating a stratum corneum (SC) layer when contacted therewith or penetrating a cell when contacted therewith.

In one embodiment of the first aspect, the composition is capable of penetrating the stratum corneum (SC) layer and penetrating the cell.

In one embodiment of the first aspect, the amino acid sequence includes CTGSTQHQC (SEQ ID NO:7), CHSALTKHC (SEQ ID NO:8), CKTGSHNQC (SEQ ID NO:9), CMGPSSMLC (SEQ ID NO:10), CTDPNQLQC (SEQ ID NO:11), or CSTHFIDTC (SEQ ID NO:12).

In one embodiment of the first aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In one embodiment of the first aspect, the composition is capable of penetrating the cellular membrane of viable non-human animal cells.

In one embodiment of the first aspect, the composition is capable of penetrating the cellular membrane of viable human cells.

In one embodiment of the first aspect, the composition is capable of penetrating the cellular membrane of viable epidermal or dermal cells.

In one embodiment of the first aspect, the composition is capable of penetrating the cellular membrane of viable immunological cells.

In one embodiment of the first aspect, the active agent includes a macromolecule. In one embodiment, the macromolecule includes a protein. In one embodiment, the protein includes an antibody or a fragment thereof including at least one paratope.

In one embodiment of the first aspect, where the active agent includes a macromolecule, the macromolecule includes a nucleic acid. In one embodiment, the nucleic acid is DNA. In one embodiment, the nucleic acid is RNA. In one embodiment, where the nucleic acid is RNA, the RNA is interfering RNA. In one embodiment, where the RNA is interfering RNA, the interfering RNA is shRNA. In one embodiment, where the RNA is interfering RNA, the interfering RNA is miRNA. In one embodiment, where the RNA is interfering RNA, the interfering RNA is siRNA. In one embodiment, where the interfering RNA is siRNA, the siRNA is IL-10 siRNA. In one embodiment, where the interfering RNA is siRNA, the siRNA is CD86 siRNA. In one embodiment, where the interfering RNA is siRNA, the siRNA is KRT6a siRNA. In one embodiment, where the interfering RNA is siRNA, the siRNA is TNFR1 siRNA. In one embodiment, where the interfering RNA is siRNA, the siRNA is TACE siRNA. In one embodiment, where the interfering RNA is siRNA, the siRNA is a mutation-specific siRNA.

In one embodiment of the first aspect, the active agent is a pharmaceutical compound.

In one embodiment of the first aspect, the active agent includes a detectable agent. In one embodiment, where the active agent includes a detectable agent, the detectable agent includes a fluorescent label. In one embodiment, where the active agent includes a detectable agent, the detectable agent includes a radioactive label.

In one embodiment of the first aspect, the active agent is a nanoparticle.

In one embodiment of the first aspect, the active agent is a low molecular weight compound.

In one embodiment of the first aspect, the active agent is an inhibitor of IL-10 biological activity. In one embodiment, where the active agent is an inhibitor of IL-10 biological activity, the active agent is selected from an IL-10 siRNA and antibodies or fragments thereof that bind IL-10.

In one embodiment of the first aspect, the peptide is conjugated to the active agent.

In one embodiment of the first aspect, the peptide is conjugated to an active agent carrier including the active agent. In one embodiment, where the peptide is conjugated to an active agent carrier including the active agent, the active agent carrier is a liposome. In one embodiment, where the peptide is conjugated to an active agent carrier including the active agent, the active agent carrier is a nanoparticle. In one embodiment, where the peptide is conjugated to an active agent carrier including the active agent, the active agent carrier is a polymeric micelle.

In a second aspect, the present disclosure provides a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is associated with an active agent or an active agent carrier including the active agent, wherein the association results from hydrophobic, electrostatic or van der Walls interactions, and wherein the composition is capable of penetrating a stratum corneum (SC) layer when contacted therewith or penetrating a cell when contacted therewith.

In one embodiment of the second aspect, the composition is capable of penetrating the stratum corneum (SC) layer and penetrating the cell.

In one embodiment of the second aspect, the amino acid sequence includes CTGSTQHQC (SEQ ID NO:7), CHSALTKHC (SEQ ID NO:8), CKTGSHNQC (SEQ ID NO:9), CMGPSSMLC (SEQ ID NO:10), CTDPNQLQC (SEQ ID NO:11), or CSTHFIDTC (SEQ ID NO:12).

In one embodiment of the second aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In a third aspect, the present disclosure provides a composition including a peptide including an amino acid sequence including a stretch of three consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is conjugated to an active agent or an active agent carrier including the active agent, and wherein the composition is capable of penetrating a stratum corneum (SC) layer when contacted therewith or penetrating a cell when contacted therewith.

In one embodiment of the third aspect, the composition is capable of penetrating the stratum corneum (SC) layer and penetrating the cell.

In one embodiment of the third aspect, the amino acid sequence includes a stretch of four consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6).

In one embodiment of the third aspect, the amino acid sequence includes a stretch of five consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6).

In one embodiment of the third aspect, the amino acid sequence includes a stretch of six consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6).

In a fourth aspect, the present disclosure provides a composition including a peptide including an amino acid sequence including a stretch of three consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is associated with an active agent or an active agent carrier including the active agent, wherein the association results from hydrophobic, electrostatic or van der Walls interactions, and wherein the composition is capable of penetrating a stratum corneum (SC) layer when contacted therewith or penetrating a cell when contacted therewith.

In one embodiment of the fourth aspect, the composition is capable of penetrating the stratum corneum (SC) layer and penetrating the cell.

In one embodiment of the fourth aspect, the amino acid sequence includes a stretch of four consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6).

In one embodiment of the fourth aspect, the amino acid sequence includes a stretch of five consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6).

In one embodiment of the fourth aspect, the amino acid sequence includes a stretch of six consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6).

In a fifth aspect, the present disclosure provides an isolated peptide including an amino acid sequence selected from one of the following sequences: ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), and ACSTHFIDTCG (SEQ ID NO:18).

In one embodiment of the fifth aspect, the peptide includes repeat units of one or more of ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), and ACSTHFIDTCG (SEQ ID NO:18). In one embodiment, where the peptide includes repeat units of one or more of ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), and ACSTHFIDTCG (SEQ ID NO:18), the unit is repeated 2 to 50 times. In one embodiment, where the peptide includes repeat units of one or more of ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), and ACSTHFIDTCG (SEQ ID NO:18), each unit is separated by an intervening peptide sequence.

In one embodiment of the fifth aspect, the peptide is a cyclic peptide including a Cys-Cys disulfide bond.

In a sixth aspect, the present disclosure provides an isolated polypeptide including repeat units of one or more of TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) and STHFIDT (SEQ ID NO:6).

In one embodiment of the sixth aspect, the unit is repeated 2 to 50 times.

In one embodiment of the sixth aspect, each unit is separated by an intervening peptide sequence.

In a seventh aspect, the present disclosure provides an isolated polypeptide consisting essentially of repeat units of one or more of TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) and STHFIDT (SEQ ID NO:6). In one embodiment, where the isolated polypeptide consists essentially of repeat units of one or more of TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) and STHFIDT (SEQ ID NO:6).

In an eighth aspect, the present disclosure provides a method of delivering an active agent to a subject, including: administering to the subject a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is conjugated to an active agent or an active agent carrier including the active agent, and wherein the composition is capable of penetrating the stratum corneum (SC) of the subject or penetrating a cell of the subject.

In one embodiment of the eighth aspect, the composition is capable of penetrating the stratum corneum (SC) of the subject and penetrating the cell of the subject.

In one embodiment of the eighth aspect, the administration is topical administration.

In one embodiment of the eighth aspect, the amino acid sequence includes CTGSTQHQC (SEQ ID NO:7), CHSALTKHC (SEQ ID NO:8), CKTGSHNQC (SEQ ID NO:9), CMGPSSMLC (SEQ ID NO:10), CTDPNQLQC (SEQ ID NO:11), or CSTHFIDTC (SEQ ID NO:12).

In one embodiment of the eighth aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In one embodiment of the eighth aspect, the composition is capable of penetrating the cellular membrane of viable non-human animal cells.

In one embodiment of the eighth aspect, the composition is capable of penetrating the cellular membrane of viable human cells.

In one embodiment of the eighth aspect, the composition is capable of penetrating the cellular membrane of viable epidermal or dermal cells.

In one embodiment of the eighth aspect, the composition is capable of penetrating the cellular membrane of viable immunological cells.

In one embodiment of the eighth aspect, the active agent includes a macromolecule. In one embodiment, the macromolecule includes a protein. In one embodiment, the protein includes an antibody or a fragment thereof including at least one paratope.

In one embodiment of the eighth aspect, where the active agent includes a macromolecule, the macromolecule includes a nucleic acid. In one embodiment, the nucleic acid is DNA. In one embodiment, the nucleic acid is RNA. In one embodiment, where the nucleic acid is RNA, the RNA is interfering RNA. In one embodiment, where the RNA is interfering RNA, the interfering RNA is shRNA. In one embodiment, where the RNA is interfering RNA, the interfering RNA is miRNA. In one embodiment, where the RNA is interfering RNA, the interfering RNA is siRNA. In one embodiment, where the interfering RNA is siRNA, the siRNA is IL-10 siRNA. In one embodiment, where the interfering RNA is siRNA, the siRNA is CD86 siRNA. In one embodiment, where the interfering RNA is siRNA, the siRNA is KRT6a siRNA. In one embodiment, where the interfering RNA is siRNA, the siRNA is TNFR1 siRNA. In one embodiment, where the interfering RNA is siRNA, the siRNA is TACE siRNA. In one embodiment, where the interfering RNA is siRNA, the siRNA is a mutation-specific siRNA.

In one embodiment of the eighth aspect, the active agent is a pharmaceutical compound.

In one embodiment of the eighth aspect, the active agent includes a detectable agent. In one embodiment, where the active agent includes a detectable agent, the detectable agent includes a fluorescent label. In one embodiment, where the active agent includes a detectable agent, the detectable agent includes a radioactive label.

In one embodiment of the eighth aspect, the active agent is a nanoparticle.

In one embodiment of the eighth aspect, the active agent is a low molecular weight compound.

In one embodiment of the eighth aspect, the active agent is an inhibitor of IL-10 biological activity. In one embodiment, where the active agent is an inhibitor of IL-10 biological activity, the active agent is selected from an IL-10 siRNA and antibodies or fragments thereof that bind IL-10.

In one embodiment of the eighth aspect, the peptide is conjugated to the active agent.

In one embodiment of the eighth aspect, the peptide is conjugated to an active agent carrier including the active agent. In one embodiment, where the peptide is conjugated to an active agent carrier including the active agent, the active agent carrier is a liposome. In one embodiment, where the peptide is conjugated to an active agent carrier including the active agent, the active agent carrier is a nanoparticle. In one embodiment, where the peptide is conjugated to an active agent carrier including the active agent, the active agent carrier is a polymeric micelle.

In a ninth aspect, the present disclosure provides a method of delivering an active agent to a subject, including: administering to the subject a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is associated with an active agent or an active agent carrier including the active agent, wherein the association results from hydrophobic, electrostatic or van der Walls interactions, and wherein the composition is capable of penetrating the stratum corneum (SC) of the subject or penetrating a cell of the subject.

In one embodiment of the ninth aspect, the composition is capable of penetrating the stratum corneum (SC) of the subject and penetrating the cell of the subject.

In one embodiment of the ninth aspect, the administration is topical administration.

In one embodiment of the ninth aspect, the amino acid sequence includes CTGSTQHQC (SEQ ID NO:7), CHSALTKHC (SEQ ID NO:8), CKTGSHNQC (SEQ ID NO:9), CMGPSSMLC (SEQ ID NO:10), CTDPNQLQC (SEQ ID NO:11), or CSTHFIDTC (SEQ ID NO:12).

In one embodiment of the ninth aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In a tenth aspect, the present disclosure provides a method of treating a subject having a dermatological disease, including: administering to the subject a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is conjugated to a dermatological active agent or a dermatological active agent carrier including the active agent, and wherein the composition is capable of penetrating the stratum corneum (SC) of the subject or penetrating a cell of the subject.

In one embodiment of the tenth aspect, the composition is capable of penetrating the stratum corneum (SC) of the subject and penetrating the cell of the subject.

In one embodiment of the tenth aspect, the administration is topical administration.

In one embodiment of the tenth aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In an eleventh aspect, the present disclosure provides a method of treating a subject having a dermatological disease, including: administering to the subject a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is associated with a dermatological active agent or a dermatological active agent carrier including the active agent, wherein the association results from hydrophobic, electrostatic or van der Walls interactions, and wherein the composition is capable of penetrating the stratum corneum (SC) of the subject or penetrating a cell of the subject.

In one embodiment of the eleventh aspect, the composition is capable of penetrating the stratum corneum (SC) of the subject and penetrating the cell of the subject.

In one embodiment of the eleventh aspect, the administration is topical administration.

In one embodiment of the eleventh aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In a twelfth aspect, the present disclosure provides a method of treating a subject having, suspected of having or susceptible to a disorder resulting at least in part from expression of an mRNA, including administering to the subject a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is conjugated to an interfering RNA which targets the mRNA or a carrier including the interfering RNA, wherein the composition is capable of penetrating the stratum corneum (SC) of the subject or a cell of the subject, and wherein the expression of the mRNA is attenuated thereby.

In one embodiment of the twelfth aspect, the composition is capable of penetrating the stratum corneum (SC) of the subject and penetrating the cell of the subject.

In one embodiment of the twelfth aspect, the administration is topical administration.

In one embodiment of the twelfth aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In a thirteenth aspect, the present disclosure provides a method of treating a subject having, suspected of having or susceptible to a disorder resulting at least in part from expression of an mRNA, including administering to the subject a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is associated with an interfering RNA which targets the mRNA or a carrier including the interfering RNA, wherein the association results from hydrophobic, electrostatic or van der Walls interactions, wherein the composition is capable of penetrating the stratum corneum (SC) of the subject or a cell of the subject, and wherein the expression of the mRNA is attenuated thereby.

In one embodiment of the thirteenth aspect, the composition is capable of penetrating the stratum corneum (SC) of the subject and penetrating the cell of the subject.

In one embodiment of the thirteenth aspect, the administration is topical administration.

In one embodiment of the thirteenth aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In a fourteenth aspect, the present disclosure provides a method of attenuating expression of an mRNA of a subject in need thereof, including administering to the subject a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is conjugated to an siRNA targeted to the mRNA or a carrier including the siRNA targeted to the mRNA, wherein the composition is capable of penetrating the stratum corneum (SC) of the subject or a cell of the subject, and wherein the expression of the mRNA is attenuated thereby.

In one embodiment of the fourteenth aspect, the mRNA is an IL-10 mRNA and the siRNA is an IL-10 siRNA.

In one embodiment of the fourteenth aspect, the mRNA is a CD86 mRNA and the siRNA is a CD86 siRNA.

In one embodiment of the fourteenth aspect, the mRNA is a KRT6a mRNA and the siRNA is KRT6a siRNA.

In one embodiment of the fourteenth aspect, the mRNA is a TNFR1 mRNA and the siRNA is a TNFR1 siRNA.

In one embodiment of the fourteenth aspect, the mRNA is a TACE mRNA and the siRNA is a TACE siRNA.

In one embodiment of the fourteenth aspect, the composition is capable of penetrating the stratum corneum (SC) and penetrating the cell of the subject.

In one embodiment of the fourteenth aspect, the administration is topical administration.

In one embodiment of the fourteenth aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In a fifteenth aspect, the present disclosure provides a method of attenuating expression of an mRNA of a subject in need thereof, including administering to the subject a composition including a peptide including the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is associated with an siRNA targeted to the mRNA or a carrier including the siRNA targeted to the mRNA, wherein the association results from hydrophobic, electrostatic or van der Walls interactions, wherein the composition is capable of penetrating the stratum corneum (SC) of the subject or a cell of the subject, and wherein the expression of the mRNA is attenuated thereby.

In one embodiment of the fifteenth aspect, the mRNA is an IL-10 mRNA and the siRNA is an IL-10 siRNA.

In one embodiment of the fifteenth aspect, the mRNA is a CD86 mRNA and the siRNA is a CD86 siRNA.

In one embodiment of the fifteenth aspect, the mRNA is a KRT6a mRNA and the siRNA is KRT6a siRNA.

In one embodiment of the fifteenth aspect, the mRNA is a TNFR1 mRNA and the siRNA is a TNFR1 siRNA.

In one embodiment of the fifteenth aspect, the mRNA is a TACE mRNA and the siRNA is a TACE siRNA.

In one embodiment of the fifteenth aspect, the composition is capable of penetrating the stratum corneum (SC) of the subject and penetrating the cell of the subject.

In one embodiment of the fifteenth aspect, the administration is topical administration.

In one embodiment of the fifteenth aspect, the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18). In one embodiment, where the amino acid sequence includes ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), or ACSTHFIDTCG (SEQ ID NO:18), the peptide is a cyclic peptide including a Cys-Cys disulfide bond.

In a sixteenth embodiment, the present disclosure provides a composition including a peptide consisting essentially of the amino acid sequence TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) or STHFIDT (SEQ ID NO:6), wherein the peptide is conjugated to an active agent or an active agent carrier including the active agent, and wherein the composition is capable of penetrating a stratum corneum (SC) layer when contacted therewith or penetrating a cell when contacted therewith.

Other aspects and embodiments will be readily apparent to the ordinarily skilled artisan upon reading the present specification.

DEFINITIONS

Figure 1:
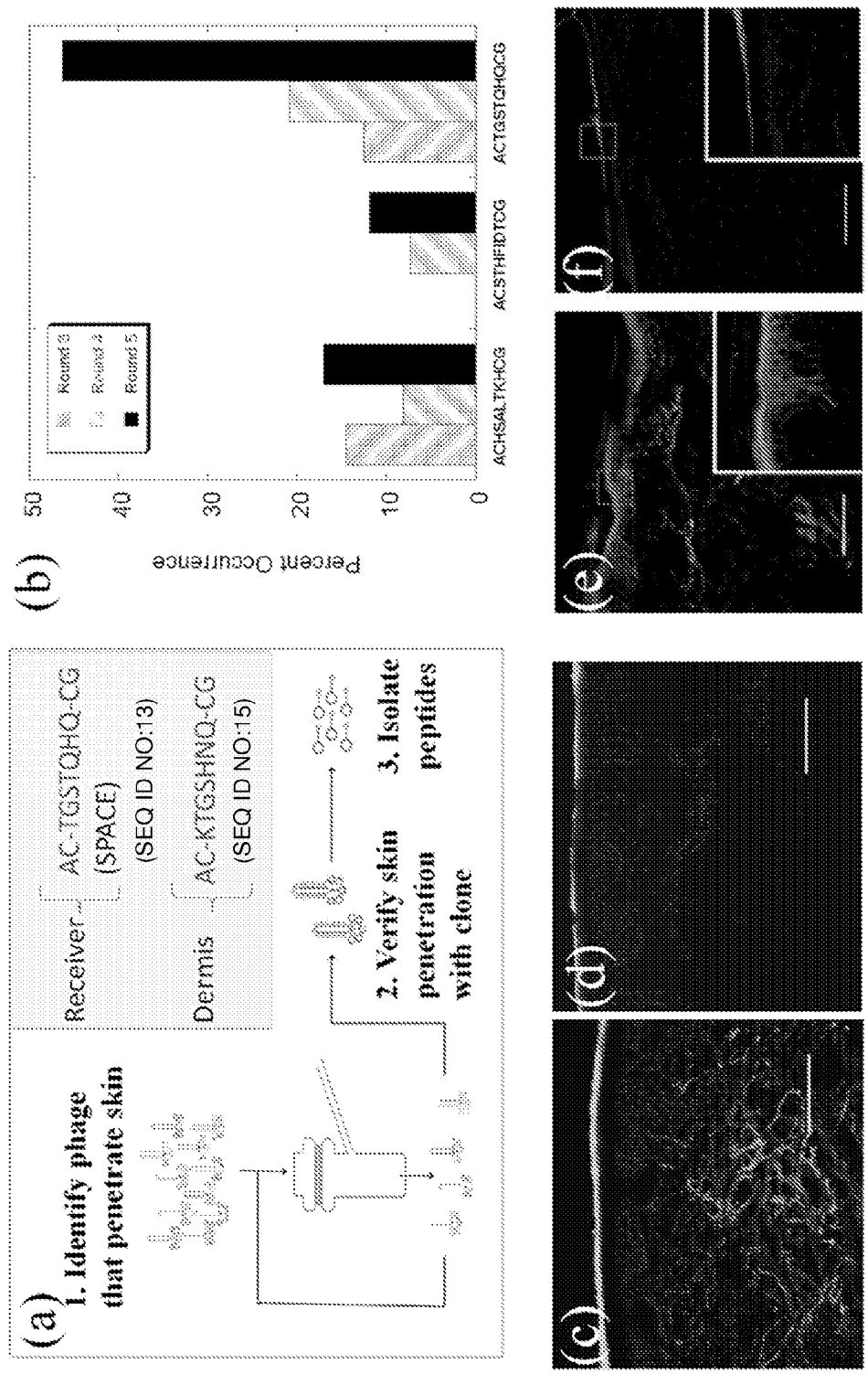
FIG. 1 shows the identification of skin penetrating peptides through in vitro phage display in porcine skin. (a) Phage library was applied in the donor compartment of a FDC. Phage found to penetrate through skin into the receiver compartment were collected, amplified, and used for the subsequent rounds of screening. The skin penetrating ability of individual clones was confirmed through diffusion experiments and confocal microscopy. To confirm the peptide's ability to penetrate skin, the peptide was isolated from the phage and its penetration into skin was confirmed visually through confocal microscopy, (b) Percentage of occurrence for each high frequency peptide sequence from Rounds 3 through 5 of the phage display screen, (c,d) Confocal microscopy images of the skin penetration profiles of SPACE and control peptide into porcine skin respectively. (e,f) Skin penetration profiles of Alexa Fluor 488 labeled streptavidin conjugated to biotinylated SPACE peptide and Alexa Fluor 488 streptavidin alone respectively. Insets show zoomed in views of the sections highlighted in the main images. Scale bar=200 µm.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications and applications mentioned herein are incorporated by reference to disclose and describe the methods and/or materials in connection with which the publications are cited. To the extent any of the applications or publications incorporated by reference herein conflict with the instant disclosure, the instant disclosure controls.

It must be noted that as used herein and in the appended claims, the singular forms "a", "and", and "the" include plural referents unless the context clearly dictates otherwise. Thus, for example, reference to "a peptide" includes a plurality of such peptides and reference to the "agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated that throughout this present disclosure reference is made to amino acids according to the single letter or three letter code. For the reader's convenience, the single and three letter amino acid code is provided below:

| G | Glycine | Gly | P | Proline | Pro |
|---|---------|-----|---|---------|-----|
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "active agent" means an agent, e.g., a protein, peptide, nucleic acid (including, e.g., nucleotides, nucleosides and analogues thereof) or small molecule drug, that provides a desired pharmacological effect upon administration to a subject, e.g., a human or a non-human animal, either alone or in combination with other active or inert components. Included in the above definition are precursors, derivatives, analogues and prodrugs of active agents. The term "active agent" may also be used herein to refer generally to any agent, e.g., a protein, peptide, nucleic acid (including, e.g., nucleotides, nucleosides and analogues thereof) or small molecule drug, conjugated or associated with a penetrating peptide as described herein or attached to or encompassed by an active agent carrier as described herein.

The term "conjugated" as used in the context of the penetrating peptide compositions described herein refers to a covalent or ionic interaction between two entities, e.g., molecules, compounds or combinations thereof.

The term "associated" as used in the context of the penetrating peptide compositions described herein refers to a non-covalent interaction between two entities, e.g., molecules, compounds or combinations thereof mediated by one or more of hydrophobic, electrostatic, and van der Walls interactions.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. Also encompassed by the terms are Fab', Fv, F(ab')$_2$, and other antibody fragments that retain specific binding to antigen.

Antibodies may exist in a variety of other forms including, for example, Fv, Fab, and (Fab')$_2$, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. U.S.A.,* 85, 5879-5883 (1988) and Bird et al., Science, 242, 423-426 (1988), which are incorporated herein by reference). (See, generally, Hood et al., *Immunology,* Benjamin, N.Y., 2nd ed. (1984), and Hunkapiller and Hood, *Nature,* 323, 15-16 (1986).

The terms "nucleic acid", "nucleic acid molecule" and "polynucleotide" are used interchangeably and refer to a polymeric form of nucleotides of any length, either deoxyribonucleotides or ribonucleotides, or analogs thereof. The terms encompass, e.g., DNA, RNA and modified forms thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

"RNA interference" (RNAi) is a process by which double-stranded RNA (dsRNA) is used to silence gene expression. Without intending to be bound by any particular theory, RNAi begins with the cleavage of longer dsRNAs into small interfering RNAs (siRNAs) by dicer, an RNaseIII-like enzyme. siRNAs are dsRNAs that are generally about 19 to 28 nucleotides, or 20 to 25 nucleotides, or 21 to 23 nucleotides in length and often contain 2-3 nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. The siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA may be designed (e.g., via decreased siRNA duplex stability at the 5' end of the antisense strand) to favor incorporation of the antisense strand into RISC.

RISC-mediated cleavage of mRNAs having a sequence at least partially complementary to the guide strand leads to a decrease in the steady state level of that mRNA and of the corresponding protein encoded by the mRNA. Alternatively, RISC can also decrease expression of the corresponding protein via translational repression without cleavage of the target mRNA. Other RNA molecules can interact with RISC and silence gene expression. Examples of other RNA molecules that can interact with RISC include short hairpin RNAs (shRNAs), single-stranded siRNAs, microRNAs (miRNAs), and dicer-substrate 27-mer duplexes, RNA molecules containing one or more chemically modified nucleotides, one or more deoxyribonucleotides, and/or one or more non-phosphodiester linkages. The term "siRNA" as used herein refers to a double-stranded interfering RNA unless otherwise noted. For purposes of the present discussion, all RNA molecules that can interact with RISC and participate in RISC-mediated changes in gene expression will be referred to as "interfering RNAs." siRNAs, shRNAs, miRNAs, and dicer-substrate 27-mer duplexes are, therefore, subsets of "interfering RNAs.

A "substitution" results from the replacement of one or more amino acids or nucleotides by different amino acids or nucleotides, respectively as compared to an amino acid sequence or nucleotide sequence of a polypeptide. If a substitution is conservative, the amino acid that is substituted into a polypeptide has similar structural or chemical properties (e.g., charge, polarity, hydrophobicity, and the like) to the amino acid that it is substituting. Conservative substitutions of naturally occurring amino acids usually result in a substitution of a first amino acid with second amino acid from the same group as the first amino acid, where exemplary amino acid groups are as follows: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral non-polar amino acids such as alanine, leucine, isoleucine, valine, proline, phenylalanine, tryptophan, and methionine. In some embodiments, polypeptide variants may have "non-conservative" changes, where the substituted amino acid differs in structural and/or chemical properties.

A "deletion" is defined as a change in either amino acid or nucleotide sequence in which one or more amino acid or nucleotide residues, respectively, are absent as compared to an amino acid sequence or nucleotide sequence of a naturally occurring polypeptide. In the context of a polypeptide or polynucleotide sequence, a deletion can involve deletion of 2, 5, 10, up to 20, up to 30 or up to 50 or more amino acids, taking into account the length of the polypeptide or polynucleotide sequence being modified.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide. "Insertion" generally refers to addition to one or more amino acid residues within an amino acid sequence of a polypeptide, while "addition" can be an insertion or refer to amino acid residues added at the N- or C-termini. In the context of a polypeptide or polynucleotide sequence, an insertion or addition may be of up to 10, up to 20, up to 30 or up to 50 or more amino acids.

"Non-native", "non-endogenous", and "heterologous", in the context of a polypeptide, are used interchangeably herein to refer to a polypeptide having an amino acid sequence or, in the context of an expression system or a viral particle, present in an environment different to that found in nature.

"Exogenous" in the context of a nucleic acid or polypeptide is used to refer to a nucleic acid or polypeptide that has been introduced into a host cell. "Exogenous" nucleic acids and polypeptides can be native or non-native to the host cell, where an exogenous, native nucleic acid or polypeptide provides for elevated levels of the encoded gene product or polypeptide in the recombinant host cell relative to that found in the host cell prior to introduction of the exogenous molecule.

As used herein, the terms "determining," "measuring," "assessing," and "assaying" are used interchangeably and include both quantitative and qualitative determinations.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, 75% free, or 90% free from other components with which it is naturally associated.

A "coding sequence" or a sequence that "encodes" a selected polypeptide, is a nucleic acid molecule which is transcribed (in the case of DNA) and translated (in the case of mRNA) into a polypeptide, for example, in-vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a gene product, such as a polypeptide. Where the gene product is a polypeptide, the polypeptide sequence or a portion thereof contains an amino acid sequence of at least 3 to 5 amino acids, 8 to 10 amino acids, or at least 15 to 20 amino acids from a polypeptide encoded by the nucleic acid sequence.

"Operably linked" refers to an arrangement of elements wherein the components so described are configured so as to perform their usual function. In the case of a promoter, a promoter that is operably linked to a coding sequence will have an effect on the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes including non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" includes any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics,* 2:482-489 (1981). This algorithm can be applied to amino acid sequences by using the scoring matrix developed by Dayhoff, *Atlas of Protein Sequences and Structure,* M. O. Dayhoff ed., 5 suppl. 3:353-358, National Biomedical Research Foundation, Washington, D.C., USA, and normalized by Gribskov, *Nucl. Acids Res.* 14(6):6745-6763 (1986).

An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address located by placing http:// in front of blast.ncbi.nlm.nih.gov/Blast.cgi.

Alternatively, in the context of polynucleotides, homology can be determined by hybridization of polynucleotides under conditions that form stable duplexes between homologous regions, followed by digestion with single-stranded-specific nuclease(s), and size determination of the digested fragments.

Two DNA, or two polypeptide sequences are "substantially homologous" to each other when the sequences exhibit at least about 80%-85%, at least about 85%-90%, at least about 90%-95%, or at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook and Russel, *Molecular Cloning: A Laboratory Manual Third Edition,* (2001) Cold Spring Harbor Laboratory Press, Cold Spring Harbor, N.Y.

A first polynucleotide is "derived from" a second polynucleotide if it has the same or substantially the same nucleotide sequence as a region of the second polynucleotide, its cDNA, complements thereof, or if it displays sequence identity as described above. This term is not meant to require or imply the polynucleotide must be obtained from the origin cited (although such is encompassed), but rather can be made by any suitable method.

A first polypeptide (or peptide) is "derived from" a second polypeptide (or peptide) if it is (i) encoded by a first polynucleotide derived from a second polynucleotide, or (ii) displays sequence identity to the second polypeptides as described above. This term is not meant to require or imply the polypeptide must be obtained from the origin cited (although such is encompassed), but rather can be made by any suitable method.

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a penetrating peptide composition that can elicit an immune response or confer immunity in the absence of a disease condition, e.g., in the case of a vaccine.

"Subject", "host" and "patient" are used interchangeably herein, to refer to an animal, human or non-human, amenable to therapy according to the methods of the disclosure or to which a peptide composition according to the present disclosure may be administered to achieve a desired effect. Generally, the subject is a mammalian subject.

The term "dermatitis," as used herein, refers to inflammation of the skin and includes, for example, allergic contact dermatitis, urticaria, asteatotic dermatitis (dry skin on the lower legs), atopic dermatitis, contact dermatitis including irritant contact dermatitis and urushiol-induced contact dermatitis, eczema, gravitational dermatitis, nummular dermatitis, otitis externa, perioral dermatitis, and seborrhoeic dermatitis.

The term "stratum corneum" refers to the horny outer layer of the epidermis, consisting of several layers of flat, keratinized, nonnucleated, dead or peeling cells.

As used in the claims, the term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, the peptides of the presently disclosed subject matter in some embodiments can "consist essentially of" a core amino acid sequence, which means that the peptide can include one or more (e.g., 1, 2, 3, 4, 5, 6, or more) N-terminal and/or C-terminal amino acids the presence of which does not materially affect the desired biological activity of the peptide.

With respect to the terms "comprising", "consisting essentially of", and "consisting of", where one of these three terms is used herein, the presently disclosed subject matter can include the use of either of the other two terms. For example, the presently disclosed subject matter relates in some embodiments to compositions comprising the amino acid sequence TGSTQHQ (SEQ ID NO:1). It is understood that the presently disclosed subject matter thus also encompasses peptides that in some embodiments consist essentially of the amino acid sequence TGSTQHQ (SEQ ID NO:1); as well as peptides that in some embodiments consist of the amino acid sequence TGSTQHQ (SEQ ID NO:1). Similarly, it is also understood that the methods of the presently disclosed subject matter in some embodiments comprise the steps that are disclosed herein and/or that are recited in the claims, that they in some embodiments consist essentially of the steps that are disclosed herein and/or that are recited in the claims, and that they in some embodiments consist of the steps that are disclosed herein and/or that are recited in the claim.

DETAILED DESCRIPTION OF EXEMPLARY EMBODIMENTS OF THE INVENTION

The disclosure is directed to peptides which both alone and when conjugated to or associated with an active agent or an active agent carrier are capable of penetrating the SC and/or the cellular membranes of viable cells such as epidermal and dermal cells. Related compositions and methods are also described herein.

Penetrating Peptides

The present disclosure provides peptides that are capable of penetrating the SC and/or penetrating viable cells following administration. These peptides are referred to herein as "penetrating peptides". In some embodiments, these penetrating peptides are capable of penetrating the cellular membranes of viable epidermal and dermal cells. Penetrating peptides according to the present disclosure may include, for example, one or more of the amino acid sequences provided in Table 1 below.

TABLE 1

| | |
|---|---|
| TGSTQHQ | (SEQ ID NO: 1) |
| HSALTKH | (SEQ ID NO: 2) |
| KTGSHNQ | (SEQ ID NO: 3) |
| MGPSSML | (SEQ ID NO: 4) |
| TDPNQLQ | (SEQ ID NO: 5) |
| STHFIDT | (SEQ ID NO: 6) |
| CTGSTQHQC | (SEQ ID NO: 7) |
| CHSALTKHC | (SEQ ID NO: 8) |
| CKTGSHNQC | (SEQ ID NO: 9) |
| CMGPSSMLC | (SEQ ID NO: 10) |
| CTDPNQLQC | (SEQ ID NO: 11) |
| CSTHFIDTC | (SEQ ID NO: 12) |
| ACTGSTQHQCG | (SEQ ID NO: 13) |
| ACHSALTKHCG | (SEQ ID NO: 14) |
| ACKTGSHNQCG | (SEQ ID NO: 15) |
| ACMGPSSMLCG | (SEQ ID NO: 16) |
| ACTDPNQLQCG | (SEQ ID NO: 17) |
| ACSTHFIDTCG | (SEQ ID NO: 18) |

In some embodiments, penetrating peptides according to the present disclosure include an amino acid sequence including a stretch of three, four, five, six, or seven consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) and STHFIDT (SEQ ID NO:6).

In some embodiments, penetrating peptides according to the present disclosure have an amino acid sequence from 8 to 11, 12 to 15, or 16 to 19 amino acids in length, including an amino acid sequence selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) and STHFIDT (SEQ ID NO:6). In some embodiments, penetrating peptides according to the present disclosure have an amino acid sequence of at least 10, at least 20, at least 30, at least 40, at least 50, at least 60, at least 70, at least 80, at least 90, or at least 100 amino acids. Penetrating peptides according to the present disclosure may be circularized by any of a variety of known cross-linking methods. In some embodiments, a penetrating peptide according to the present disclosure may be provided in a circularized conformation (i.e., as a cyclic peptide) in which a Cys-Cys disulfide bond is present. In some embodiments, penetrating peptides according to the present disclosure have an amino acid sequence including an internal amino acid sequence selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) and STHFIDT (SEQ ID NO:6), wherein the amino acid sequence of the peptide includes at least a first Cys positioned external to the internal sequence in the N-terminal direction and at least a second Cys positioned external to the internal sequence in the C-terminal direction.

In some embodiments, penetrating peptides according to the present disclosure include an amino acid sequence including an internal stretch of three, four, five, or six consecutive amino acids selected from one of the following amino acid sequences TGSTQHQ (SEQ ID NO:1), HSALTKH (SEQ ID NO:2), KTGSHNQ (SEQ ID NO:3), MGPSSML (SEQ ID NO:4), TDPNQLQ (SEQ ID NO:5) and STHFIDT (SEQ ID NO:6); and further including at least a first Cys positioned external to the internal sequence in the N-terminal direction and at least a second Cys positioned external to the internal sequence in the C-terminal direction.

The penetrating peptides disclosed herein include those having the amino acid sequences provided, as well as peptides having one or more amino acid substitutions, e.g., one or more conservative amino acid substitutions, relative to the sequences provided, wherein the peptides retains the capability of penetrating the SC or penetrating a cell.

Active Agents

The ability of the above peptides to penetrate the SC following topical administration and/or to penetrate the cellular membranes of viable cells, e.g., epidermal and dermal cells, while conjugated to or associated with a molecular cargo, e.g., a low molecular weight compound or macromolecule, makes them suitable for facilitating the delivery of a wide variety of active agents known in the art.

General classes of active agents which may be delivered include, for example, proteins, peptides, nucleic acids, nucleotides, nucleosides and analogues thereof; as well as pharmaceutical compounds, e.g., low molecular weight compounds.

Active agents which may be delivered using the penetrating peptides disclosed herein include agents which act on the peripheral nerves, adrenergic receptors, cholinergic receptors, the skeletal muscles, the cardiovascular system, smooth muscles, the blood circulatory system, synaptic sites, neuroeffector junction sites, endocrine and hormone systems, the immunological system, the reproductive system, the skeletal system, autacoid systems, the alimentary and excretory systems, the histamine system and the central nervous system.

Suitable active agents may be selected, for example, from dermatological agents, anti-neoplastic agents, cardiovascular agents, renal agents, gastrointestinal agents, rheumatologic agents, immunological agents, and neurological agents among others.

Suitable dermatological agents may include, for example, local anesthetics, anti-inflammatory agents, anti-infective agents, agents to treat acne, anti-virals, anti-fungals, agents for psoriasis such as topical corticosteroids among others.

In some embodiments, a suitable dermatological agent is selected from the following list: 16-17A-Epoxyprogesterone (CAS Registry Number: 1097-51-4), P-methoxycinnamic acid/4-Methoxycinnamic acid (CAS Registry Number: 830-09-1), Octyl Methoxycinnamate (CAS Registry Number: 5466-77-3), Octyl Methoxycinnamate (CAS Registry Number: 5466-77-3), Methyl p-methoxy cinnamate (CAS Registry Number: 832-01-9), 4-ESTREN-17β-OL-3-ONE (CAS Registry Number: 62-90-8), Ethyl-p-anisoyl acetate (CAS Registry Number: 2881-83-6), Dihydrouracil (CAS Registry Number: 1904-98-9), Lopinavir (CAS Registry Number: 192725-17-0), RITANSERIN(CAS Registry Number: 87051-43-2), Nilotinib (CAS Registry Number: 641571-10-0); Rocuronium bromide (CAS Registry Number: 119302-91-9), p-Nitrobenzyl-6-(1-hydroxyethyl)-1-azabicyclo (3.2.0)heptane-3,7-dione-2-carboxylate (CAS Registry Number: 74288-40-7), Abamectin (CAS Registry Number: 71751-41-2), Paliperidone (CAS Registry Number: 144598-75-4), Gemifloxacin (CAS Registry Number: 175463-14-6), Valrubicin (CAS Registry Number: 56124-62-0), Mizoribine (CAS Registry Number: 50924-49-7), Solifenacin succinate (CAS Registry Number: 242478-38-2), Lapatinib (CAS Registry Number: 231277-92-2), Dydrogesterone (CAS Registry Number: 152-62-5), 2,2-Dichloro-N-[(1R,2S)-3-fluoro-1-hydroxy-1-(4-methylsulfonylphenyl)propan-2-yl]acetamide (CAS Registry Number: 73231-34-2), Tilmicosin (CAS Registry Number: 108050-54-0), Efavirenz (CAS Registry Number: 154598-52-4), Pirarubicin (CAS Registry Number: 72496-41-4), Nateglinide (CAS Registry Number: 105816-04-4), Epirubicin (CAS Registry Number: 56420-45-2), Entecavir (CAS Registry Number: 142217-69-4), Etoricoxib (CAS Registry Number: 202409-33-4), Cilnidipine (CAS Registry Number: 132203-70-4), Doxorubicin hydrochloride (CAS Registry Number: 25316-40-9), Escitalopram (CAS Registry Number: 128196-01-0), Sitagliptin phosphate monohydrate (CAS Registry Number: 654671-77-9), Acitretin (CAS Registry Number: 55079-83-9), Rizatriptan benzoate (CAS Registry Number: 145202-66-0), Doripenem (CAS Registry Number: 148016-81-3), Atracurium besylate (CAS Registry Number: 64228-81-5), Nilutamide (CAS Registry Number: 63612-50-0), 3,4-Dihydroxyphenylethanol (CAS Registry Number: 10597-60-1), KETANSERIN TARTRATE (CAS Registry Number: 83846-83-7), Ozagrel (CAS Registry Number: 82571-53-7), Eprosartan mesylate (CAS Registry Number: 144143-96-4), Ranitidine hydrochloride (CAS Registry Number: 66357-35-5), 6,7-Dihydro-6-mercapto-5H-pyrazolo[1,2-a][1,2,4]triazolium chloride (CAS Registry Number: 153851-71-9), Sulfapyridine (CAS Registry Number: 144-83-2), Teicoplanin (CAS Registry Number: 61036-62-2), Tacrolimus (CAS Registry Number: 104987-11-3), LUMIRACOXIB (CAS Registry Number: 220991-20-8), Allyl alcohol (CAS Registry Number: 107-18-6), Protected meropenem (CAS Registry Number: 96036-02-1), Nelarabine (CAS Registry Number: 121032-29-9), Pimecrolimus (CAS Registry Number: 137071-32-0), 4-[6-Methoxy-7-(3-piperidin-1-ylpropoxy)quinazolin-4-yl]-N-(4-propan-2-yloxyphenyl)piperazine-1-carboxamide (CAS Registry Number: 387867-13-2), Ritonavir (CAS Registry Number: 155213-67-5), Adapalene (CAS Registry Number: 106685-40-9), Aprepitant (CAS Registry Number: 170729-80-3), Eplerenone (CAS Registry Number: 107724-20-9), Rasagiline mesylate (CAS Registry Number: 161735-79-1), Miltefosine (CAS Registry Number: 58066-85-6), Raltegravir potassium (CAS Registry Number: 871038-72-1), Dasatinib monohydrate (CAS Registry Number: 863127-77-9), OXOMEMAZINE (CAS Registry Number: 3689-50-7), Pramipexole (CAS Registry Number: 104632-26-0), PARECOXIB SODIUM (CAS Registry Number: 198470-85-8), Tigecycline (CAS Registry Number: 220620-09-7), Toltrazuril (CAS Registry Number: 69004-03-1), Vinflunine (CAS Registry Number: 162652-95-1), Drospirenone (CAS Registry Number: 67392-87-4), Daptomycin (CAS Registry Number: 103060-53-3), Montelukast sodium (CAS Registry Number: 151767-02-1), Brinzolamide (CAS Registry Number: 138890-62-7), Maraviroc (CAS Registry Number: 376348-65-1), Doxercalciferol (CAS Registry Number: 54573-75-0), Oxolinic acid (CAS Registry Number: 14698-29-4), Daunorubicin hydrochloride (CAS Registry Number: 23541-50-6), Nizatidine (CAS Registry Number: 76963-41-2), Idarubicin (CAS Registry Number: 58957-92-9), FLUOXETINE HYDROCHLORIDE (CAS Registry Number: 59333-67-4), Ascomycin (CAS Registry Number: 11011-38-4), beta-Methyl vinyl phosphate (MAP) (CAS Registry Number: 90776-59-3), Amorolfine (CAS Registry Number: 67467-83-8), Fexofenadine HCl (CAS Registry Number: 83799-24-0), Ketoconazole (CAS Registry Number: 65277-42-1), 9,10-difluoro-2,3-dihydro-3-me-7-oxo-7H-pyrido-1 (CAS Registry Number: 82419-35-0), Ketoconazole (CAS Registry Number: 65277-42-1), Terbinafine HCl (CAS Registry Number: 78628-80-5), Amorolfine (CAS Registry Number: 78613-35-1), Methoxsalen (CAS Registry Number: 298-81-7), Olopatadine HCl (CAS Registry Number: 113806-05-6), Zinc Pyrithione (CAS Registry Number: 13463-41-7), Olopatadine HCl (CAS Registry Number: 140462-76-6), Cyclosporine (CAS Registry Number: 59865-13-3), and Botulinum toxin and its analogs and vaccine components.

Protein, Polypeptides and Peptides as Active Agents

Proteins useful in the disclosed depot formulations may include, for example, molecules such as cytokines and their receptors, as well as chimeric proteins including cytokines or their receptors, including, for example tumor necrosis factor alpha and beta, their receptors and their derivatives; renin; growth hormones, including human growth hormone, bovine growth hormone, methione-human growth hormone, des-phenylalanine human growth hormone, and porcine growth hormone; growth hormone releasing factor (GRF); parathyroid and pituitary hormones; thyroid stimulating hormone; human pancreas hormone releasing factor; lipoproteins; colchicine; prolactin; corticotrophin; thyrotropic hormone; oxytocin; vasopressin; somatostatin; lypressin; pancreozymin; leuprolide; alpha-1-antitrypsin; insulin A-chain; insulin B-chain; proinsulin; follicle stimulating hormone; calcitonin; luteinizing hormone; luteinizing hormone releasing hormone (LHRH); LHRH agonists and antagonists; glucagon; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; gonadotropin releasing hormone; bovine somatotropin; porcine somatotropin; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, 4, -5, or -6 (NT-3, NT-4, NT-5, or NT-6), or a nerve growth factor such as NGF-β; platelet-derived growth factor (PDGF); fibroblast growth factor such as acidic FGF and basic FGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha (e.g., interferonα2A), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV-1 envelope glycoprotein, gp120, gp160 or fragments thereof; transport proteins; homing receptors; addressins; fertility inhibitors such as the prostaglandins; fertility promoters; regulatory proteins; antibodies (including fragments thereof) and chimeric proteins, such as immunoadhesins; precursors, derivatives, prodrugs and analogues of these compounds, and pharmaceutically acceptable salts of these compounds, or their precursors, derivatives, prodrugs and analogues.

Suitable proteins or peptides may be native or recombinant and include, e.g., fusion proteins.

In some embodiments, the protein is a growth hormone, such as human growth hormone (hGH), recombinant human growth hormone (rhGH), bovine growth hormone, methione-human growth hormone, des-phenylalanine human growth hormone, and porcine growth hormone; insulin, insulin A-chain, insulin B-chain, and proinsulin; or a growth factor, such as vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

Suitable peptides for use as the active agent in the injectable, biodegradable delivery depots disclosed herein include, but are not limited to, Glucagon-like peptide-1 (GLP-1) and precursors, derivatives, prodrugs and analogues thereof.

Nucleic Acids as Active Agents

Nucleic acid active agents include nucleic acids as well as precursors, derivatives, prodrugs and analogues thereof, e.g., therapeutic nucleotides, nucleosides and analogues thereof; therapeutic oligonucleotides; and therapeutic polynucleotides. Active agents selected from this group may find particular use as anticancer agents and antivirals. Suitable nucleic acid active agents may include for example ribozymes, antisense oligodeoxynucleotides, aptamers and siRNA. Examples of suitable nucleoside analogues include, but are not limited to, cytarabine (araCTP), gemcitabine (dFdCTP), and floxuridine (FdUTP). In some embodiments, a suitable nucleic acid active agent is an interfering RNA, e.g., shRNA, miRNA or siRNA. Suitable siRNAs include, for example, IL-7 (Interleukin-7) siRNA, IL-10 (Interleukin-10) siRNA, IL-22 (Interleukin-22) siRNA, IL-23 (Interleukin 23) siRNA, CD86 siRNA, KRT6a (keratin 6A) siRNA, K6a N171K (keratin 6a N171K) siRNA, TNFα (tumor necrosis factor α) siRNA, TNFR1 (tumor necrosis factor receptor-1) siRNA, TACE (tumor necrosis factor (TNF)-α converting enzyme) siRNA, RRM2 (ribonucleotide reductase subunit-2) siRNA, and VEGF (vascular endothelial growth factor) siRNA. mRNA sequences of the human gene targets of these siRNAs are known in the art. For IL-7, see, e.g., GenBank Accession: NM_000880.3, GenBank Accession: NM_001199886.1, GenBank Accession: NM_001199887.1, and GenBank Accession: NM_001199888.1; for IL-10, see, e.g., GenBank Accession: NM_000572.2; for IL-22 see, e.g., GenBank Accession: NM_020525.4; for IL-23, see, e.g., GenBank Accession: NM_016584.2, and GenBank Accession: AF301620.1; for CD86, see, e.g., GenBank Accession: NM_175862.4, GenBank Accession: NM_006889.4, GenBank Accession: NM_176892.1, GenBank Accession: NM_001206924.1, and GenBank Accession: NM_001206925.1; for KRT6a, see, e.g., GenBank Accession: NM_005554.3; for TNFα, see, e.g., GenBank Accession: NM_000594.2; for TNFR1, see, e.g., GenBank Accession: NM_001065.3; for TACE, see, e.g., GenBank Accession: NM_003183.4; for RRM2, see, e.g., GenBank Accession: NM_001165931.1 and GenBank Accession: NM_001034.3; for VEGF, see, e.g., GenBank Accession: NM_001025366.2, GenBank Accession: NM_001025367.2, GenBank Accession: NM_001025368.2, GenBank Accession: NM_001025369.2, GenBank Accession: NM_001025370.2, NM_001033756.2, GenBank Accession: NM_001171622.1, and GenBank Accession: NM_003376.5.

In addition a variety of methods and techniques are known in the art for selecting a particular mRNA target sequence during siRNA design. See, e.g., the publicly available siRNA design tool provided by the Whitehead Institute of Biomedical Research at MIT. This tool can be located on the internet on the website located by placing http:// directly preceding jura.wi.mit.edu/bioc/siRNAext/.

Additional Active Agent Compounds

A variety of additional active agent compounds may be used in the injectable depot compositions disclosed herein. Suitable compounds may include compounds directed to one or more of the following drug targets: Kringle domain, Carboxypeptidase, Carboxylic ester hydrolases, Glycosylases, Rhodopsin-like dopamine receptors, Rhodopsin-like adrenoceptors, Rhodopsin-like histamine receptors, Rhodopsin-like serotonin receptors, Rhodopsin-like short peptide receptors, Rhodopsin-like acetylcholine receptors, Rhodopsin-like nucleotide-like receptors, Rhodopsin-like lipid-like ligand receptors, Rhodopsin-like melatonin receptors, Metalloprotease, Transporter ATPase, Carboxylic ester hydrolases, Peroxidase, Lipoxygenase, DOPA decarboxylase, A/G cyclase, Methyltransferases, Sulphonylurea receptors, other transporters (e.g., Dopamine transporter, GABA transporter 1, Norepinephrine transporter, Potassium-transporting ATPase α-chain 1, Sodium-(potassium)-chloride cotransporter 2, Serotonin transporter, Synaptic vesicular amine transporter, and Thiazide-sensitive sodium-chloride cotransporter), Electrochemical nucleoside transporter, Voltage-gated ion channels, GABA receptors (Cys-Loop), Acetylcholine receptors (Cys-Loop), NMDA receptors, 5-HT3 receptors (Cys-Loop), Ligand-gated ion channels Glu: kainite, AMPA Glu receptors, Acid-sensing ion channels aldosterone, Ryanodine receptors, Vitamin K epoxide reductase, MetGluR-like GABA$_B$ receptors, Inwardly rectifying K$^+$ channel, NPC1L1, MetGluR-like calcium-sensing receptors, Aldehyde dehydrogenases, Tyrosine 3-hydroxylase, Aldose reductase, Xanthine dehydrogenase, Ribonucleoside reductase, Dihydrofolate reductase, IMP dehydrogenase, Thioredoxin reductase, Dioxygenase, Inositol monophosphatase, Phosphodiesterases, Adenosine deaminase, Peptidylprolyl isomerases, Thymidylate synthase, Aminotransferases, Farnesyl diphosphate synthase, Protein kinases, Carbonic anhydrase, Tubulins, Troponin, Inhibitor of IκB kinase-β, Amine oxidases, Cyclooxygenases, Cytochrome P450s, Thyroxine 5-deiodinase, Steroid dehydrogenase, HMG-CoA reductase, Steroid reductases, Dihydroorotate oxidase, Epoxide hydrolase, Transporter ATPase, Translocator, Glycosyltransferases, Nuclear receptors NR3 receptors, Nuclear receptors: NR1 receptors, and Topoisomerase.

In some embodiments, the active agent is a compound targeting one of rhodopsin-like GPCRs, nuclear receptors, ligand-gated ion channels, voltage-gated ion channels, penicillin-binding protein, myeloperoxidase-like, sodium: neurotransmitter symporter family, type II DNA topoisomerase, fibronectin type III, and cytochrome P450.

In some embodiments, the active agent is an anticancer agent. Suitable anticancer agents include, but are not limited to, Actinomycin D, Alemtuzumab, Allopurinol sodium, Amifostine, Amsacrine, Anastrozole, Ara-CMP, Asparaginase, Azacytadine, Bendamustine, Bevacizumab, Bicalutimide, Bleomycin (e.g., Bleomycin A$_2$ and B$_2$), Bortezomib, Busulfan, Camptothecin sodium salt, Capecitabine, Carboplatin, Carmustine, Cetuximab, Chlorambucil, Cisplatin, Cladribine, Clofarabine, Cyclophosphamide, Cytarabine, Dacarbazine, Dactinomycin, Daunorubicin, Daunorubicin liposomal, Dacarbazine, Decitabine, Docetaxel, Doxorubicin, Doxorubicin liposomal, Epirubicin, Estramustine, Etoposide, Etoposide phosphate, Exemestane, Floxuridine, Fludarabine, Fludarabine phosphate, 5-Fluorouracil, Fotemustine, Fulvestrant, Gemcitabine, Goserelin, Hexamethylmelamine, Hydroxyurea, Idarubicin, Ifosfamide, Imatinib, Irinotecan, Ixabepilone, Lapatinib, Letrozole, Leuprolide acetate, Lomustine, Mechlorethamine, Melphalan, 6-Mercaptopurine, Methotrexate, Mithramycin, Mitomycin C, Mitotane, Mitoxantrone, Nimustine, Ofatumumab, Oxaliplatin, Paclitaxel, Panitumumab, Pegaspargase, Pemetrexed, Pentostatin, Pertuzumab, Picoplatin, Pipobroman, Plerixafor, Procarbazine, Raltitrexed, Rituximab, Streptozocin, Temozolomide, Teniposide, 6-Thioguanine, Thiotepa, Topotecan, Trastuzumab, Treosulfan, Triethylenemelamine, Trimetrexate, Uracil Nitrogen Mustard, Valrubicin, Vinblastine, Vincristine, Vindesine, Vinorelbine, and analogues, precursors, derivatives and pro-drugs thereof. It should be noted that two or more of the above compounds may be used in combination in the penetrating peptide compositions of the present disclosure.

Active agents of interest for use in the disclosed penetrating peptide compositions may also include opioids and derivatives thereof as well as opioid receptor agonists and antagonists, e.g., naltrexone, naloxone, nalbuphine, fentanyl, sufentanil, oxycodone, and pharmaceutically acceptable salts and derivatives thereof.

In some embodiments the active agent is a small molecule or low molecular weight compound, e.g., a molecule or compound having a molecular weight of less than or equal to about 1000 Daltons, e.g., less than or equal to about 800 Daltons.

In some embodiments, the active agent is a label. Suitable labels include, e.g, radioactive isotopes, fluorescers, chemiluminescers, chromophores, enzymes, enzyme substrates, enzyme cofactors, enzyme inhibitors, chromophores, dyes, metal ions, magnetic particles, nanoparticles and quantum dots.

The active agent may be present in any suitable concentration in the compositions disclosed herein. Suitable concentrations may vary depending on the potency of the active agent, active agent half-life, etc. In addition, penetrating peptide compositions according to the present disclosure may include one or more active agents, e.g., a combination of two or more of the active agents described above.

Active Agent Carriers

As described previously herein one or more active agents may be conjugated to or associated with a penetrating peptide to provide a penetrating peptide composition according to the present disclosure. Alternatively, a penetrating peptide composition according to the present disclosure may include a penetrating peptide as disclosed herein conjugated or associated with an active agent carrier which in turn includes the active agent attached thereto and/or disposed therein.

Suitable active agent carriers include, for example, liposomes, nanoparticles, micelles, microbubbles, and the like. Techniques for incorporating active agents into such carriers are known in the art. For example, liposomes or lipidic particles can be prepared in accordance with U.S. Pat. No. 5,077,057 (Szoka, Jr.). Liposomes formed from nonphosphal lipid components which have the potential to form lipid bilayers are disclosed in Biochim. Biophys. Acta., 19:227-232 (1982). For the preparation, purification, modification and loading of liposomes see generally, New, R. C. C., Liposomes: A Practical Approach, (1990) Oxford University Press Inc., N.Y.

A general discussion of techniques for preparation of liposomes and of medication encapsulating liposomes can be found in U.S. Pat. No. 4,224,179 (Schneider). See, also Mayer et al., Chemistry and Physics of Lipids, 40: 333-345 (1986). See also, U.S. Pat. No. 6,083,539 for the encapsulation of an active agent dry powder composition. For incorporation of active agents into nanoparticles, see, e.g., M. M. de Villiers et al. (editors), Nanotechnology in Drug Delivery, (2009) American Associate of Pharmaceutical Scientists. For incorporation of active agents into micelles, see, e.g., D. R. Lu and S. Oie, Cellular Drug Delivery: Principles and Practice, (2004) Humana Press Inc. Totowa, N.J.

Attachment of Peptides to Active Agents and Active Agent Carriers

Penetrating peptides as described herein may be conjugated to or associated with an active agent. Alternatively, a penetrating peptide as disclosed herein may conjugated or associated with an active agent carrier, which in turn includes the active agent attached thereto and/or disposed therein (examples of which are discussed above). Conjugation techniques generally result in the formation of one or more covalent bonds between the penetrating peptide and either the active agent or an active agent carrier while association techniques generally utilize one or more of hydrophobic, electrostatic or van der Walls interactions.

A variety of techniques may be used for conjugating or associating a peptide to an active agent. Similarly, a variety of techniques may be used for conjugating or associating a peptide to an active agent carrier, e.g., liposomes, nanoparticles, or micelle as described herein.

For example, where the active agent is a peptide or polypeptide, the entire composition, including the penetrating peptide, may be synthesized using standard amino acid synthesis techniques. Other methods including standard molecular biology techniques may be used to express and purify the entire polypeptide sequence including the penetrating peptide. Additional methods of conjugating peptides to other peptides or polypeptides include Cu-catalyzed azide/alkyne [3+2] cycloaddition "Click Chemistry" as described by Rostovtsev et al. (2002) Angew. Chem. Int. Ed. 41: 2596-2599 and Tornoe et al. (2002) J. Org. Chem. 67: 3057-3064; azide/DIFO (Difluorinated Cyclooctyne) Cu-free Click Chemistry as described by Baskin et al. (2007) PNAS Vol. 104, No. 43: 167393-16797; azide/phosphine "Staudinger Reaction" as described by Lin et al. (2005) J. Am. Chem. Soc. 127: 2686-2695; azide/triarylphosphine "Modified Staudinger Reaction" as described by Saxon and Bertozzi (2000) Mar. 17 Science 287(5460):2007-10; and catalyzed olefin cross metathesis reactions as described by Casey (2006) J. of Chem. Edu. Vol. 83, No. 2: 192-195, Lynn et al. (2000) J. Am. Chem. Soc. 122: 6601-6609, and Chen et al. (2003) Progress in Chemistry 15: 401-408.

Where the active agent is a low molecular weight compound or small molecule, a variety of techniques may be utilized to conjugate the low molecular weight compound or small molecule to a penetrating peptide as described herein, e.g., Click chemistry as described in Loh et al., Chem Commun (Camb), 2010 Nov. 28; 46(44):8407-9. Epub 2010 Oct. 7. See also, Thomson S., Methods Mol Med., (2004); 94:255-65, describing conjugation of small molecule carboxyl, hydroxyl, and amine residues to amine and sulfhydryl residues on proteins.

Methods are also available in the art for conjugating peptides to active agent carriers such as liposomes. See, for example, G. Gregoriadis (editor), Liposome Technology Third Edition, Volume II Entrapment of Drugs and Other materials into Liposomes, (2007), Informa Healthcare, New York, N.Y., which describes techniques for coupling peptides to the surface of liposomes. For the covalent attachment of proteins, to liposomes see, New, R.C.C., Liposomes: A Practical Approach, (1990) Oxford University Press Inc., N.Y. at pages 163-182.

Administration of Penetrating Peptide Compositions as Pharmaceutical Formulations One skilled in the art will appreciate that a variety of suitable methods of administering a penetrating peptide composition to a subject or host, e.g., patient, in need thereof, are available, and, although more than one route can be used to administer a particular composition, a particular route can provide a more immediate and more effective reaction than another route. Pharmaceutically acceptable excipients are also well known to those who are skilled in the art, and are readily available. The choice of excipient will be determined in part by the particular compound, as well as by the particular method used to administer the composition. Accordingly, there are a wide variety of suitable formulations of the penetrating peptide compositions. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; (d) suitable emulsions and (e) hydrogels. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are known in the art.

Penetrating peptide formulations can be made into aerosol formulations to be administered via inhalation. These aerosol formulations can be placed into pressurized acceptable propellants, In-Vitro Use In addition to treatment methods and other in-vivo uses, the penetrating peptide compositions disclosed herein may also be used in the context of in-vitro experimentation. For example, the penetrating peptides disclosed herein may be used to deliver any of a wide variety of active agents as discussed herein, as well as potential active agents, into viable cells in-vitro to determine the potential therapeutic effect, toxicity, etc. of the active agent or potential active agent. For this reason, the penetrating peptides and penetrating peptide compositions of the present disclosure may be useful in the context of drug testing and/or screening.

In some embodiments, penetrating peptide compositions as described herein may be used in in-vitro gene silencing experiments, e.g., by introducing a penetrating peptide-interfering RNA conjugate directed to a gene target and monitoring the effect on gene expression.

Additional in-vitro uses may include the use of penetrating peptides as disclosed herein conjugated or associated with one or more labeling agents (e.g., fluorescent agents or radioactive labels) or one or more labeling agent carriers in order to label viable cells in vitro.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Peptides that penetrate the SC were identified using in vitro phage display as follows and as depicted generally in FIG. 1, panel A.

Phage Display

The Ph.D.-C7C Phage Display Peptide Library (New England Biolabs) was utilized. Screening studies were performed on porcine skin in Franz Diffusion cells (FDCs, Permegear). $2\times10^{11}$ pfu (10 µL) of phage library along with 1 mL of Phosphate Buffered Saline (PBS, pH 7.4) were placed in the donor compartment of the FDC. After 24 hours, the liquid in the receiver compartment was removed and titered by adding an aliquot of the receiver solution to 200 µL of *E. Coli* strain ER2738 (New England Biolabs) and plating on IPTG/Xgal plates. The number of blue plaques formed after incubation for 18 hours at 37° C. was counted and 20 plaques were randomly selected for sequencing. For subsequent screening rounds, 1 mL of the receiver solution was added to 20 mL of a 1:100 diluted overnight culture of ER2738 and grown for 4.5 hours to amplify the phage. The phage were purified by PEG/NaCl precipitation and resuspended in PBS. The amplified phage were then used in the next round of screening. The number of phage placed in the donor compartment, $2\times10^{11}$ pfu, was held constant for all 5 rounds of screening.

Five rounds of selection led to narrowing down of the display library as depicted in FIG. 1, panel B. One sequence, AC-TGSTQHQ-CG (SEQ ID NO:13), appeared in high frequency in higher rounds and was designated as Skin Permeating And Cell Entering (SPACE) peptide. A second sequence (AC-HSALTKH-CG) (SEQ ID NO:14) also appeared in high frequency. A third sequence (AC-STHFIDT-CG) (SEQ ID NO:18) appeared in relatively high frequency in rounds 4 and 5. Note that "AC-" and "-CG" as used herein in the context of the peptide sequences indicates that the AC and CG portions of the sequence originated with the phage display system.

Phage Penetration

Penetration of various phage samples including phage with no peptide library, the entire phage library, SPACE-peptide displaying phage and heptaglycine phage was determined following the same procedure described above (without the amplification and follow-up screening steps) using the number of phage colonies detected in the receiver samples and standard equations for determining penetration.

Phage Cloning

To verify the ability of the phage to penetrate the skin, the Ph. D. Peptide Display Cloning System (M13KE vector, New England Biolabs) was used to create phage, which displayed specific peptide sequences of interest. Peptide sequences of interest were cloned into the Ph. D. Peptide Display Cloning System (M13KE vector, New England Biolabs). The peptide sequence was inserted in between the KpnI and EagI restriction sites. To differentiate the original M13KE vector from the modified M13KE vector containing the peptide insert, the reverse primer was engineered to modify the EagI restriction site (5'-CGGCCG-3') (SEQ ID NO:19) to the SacII restriction site (5'-CCGCGG-3') (SEQ ID NO:20) through two site mutations. Both the forward and reverse primers were used to replicate the entire vector. The forward primer was 5'-GTTC-CGCGGAAACTGTTGAAAGTTGTTTAGCAAAATCCC-3' (SEQ ID NO:21). The reverse primer for TGSTQHQ (SEQ ID NO:1) and THGQTQS (SEQ ID NO:22) were 5'-TTTC-CGCGGAACCTCCACCGCACTGATGCT-GCTCGAACCAGTACAAGCAGAGTGAG AATA-GAAAGGTACTACTAAAGGAATTGCGAATAATAATT-TTTTCAC-3' (SEQ ID NO:23) and 5'-TTTCCGCGGAAC-CTCCACCGCA(AGACTGAGTCTGCCCATGAGT) ACAAGCAGAGTG AGAATAGAAAGGTACTAC-TAAAGGAATTGCGAATAATAATTTTTTCAC-3' (SEQ ID NO:24) respectively.

The replication products were purified and then digested with SacII to produce the blunt ends required for ligation of the vector. The modified vector was electroporated into electrocompetent ER2738 cells and then immediately placed in 1 mL of SOC medium (New England Biolabs) and grown for 45 minutes at 37° C. The resulting culture was then placed into 50 mL of a 1:100 diluted overnight culture and grown for 4.5 hours. The amplified phage were purified using the protocol stated above and titered. Plaques were picked after 18 hours and sequenced to verify the peptide being displayed on the phage surface.

Peptide Synthesis

The peptide sequence for the SPACE peptide was ACTG-STQHQCG (SEQ ID NO:13) and the peptide sequence for the control peptide (CP) was ACTHGQTQSCG (SEQ ID NO:25) with the formation of the disulfide bond between the cysteines to produce a cyclic peptide. 5-carboxyfluorescein (5-FAM) or fluorescein isothiocyanate (FITC) conjugated peptides were synthesized by ChinaTech Peptide Co. and RS Synthesis. The dye was placed on the N-terminus of the peptide. Biotinylated versions of both peptides were synthesized by ChinaTech Peptide Co. and the peptides with no modifications were synthesized by RS Synthesis.

Example 2

Mathematical Model

Penetration of phage across the SC is unexpected given its size (Potts R O & Guy R H (1992) Predicting skin permeability. *Pharm Res* 9(5):663-669; Magnusson B, Pugh W, & Roberts M (2004) Simple rules defining the potential of compounds for transdermal delivery or toxicity. *Pharm Res* 21(6): 1047-1054; Mitragotri S (2003) Modeling skin permeability to hydrophilic and hydrophobic solutes based on four permeation pathways. *J Control Release* 86(1):69-92.). Large solutes (typically MW>500 Da) exhibit poor skin penetration and measurement of their transdermal permeation is often limited by the sensitivity of their detection. The M13 phage used in this study is a long filamentous particle, approximately 8 nm in width and 900 nm in length. High donor concentration ($\sim 2 \times 10^{11}$ pfu/ml), low detection limit ($\sim 1$ pfu) and the potential for amplification facilitated assessment of dermal penetration of phage. The measured permeability of phage across porcine skin was very low; $10^{-9}$ cm/hr for control phage (phage without the peptide library) and $10^{-7}$-$10^{-6}$ cm/hr for SPACE-phage. Permeation of phage, though much smaller than that of low molecular weight solutes, was significant and unexpected. Most importantly, penetration of phage was sequence-specific.

Diffusion through intercellular lipids represents the classical mechanism for transdermal permeation of molecules. This mechanism, however, is generally limited to small, lipophilic molecules. Permeation of large, hydrophilic molecules is relatively less studied. Transdermal transport of such solutes is attributed to two pathways; (i) polar or porous pathways and (ii) appendages (follicles). Mathematical models have been described in the literature to describe contributions of both pathways to transdermal permeation (Tang H, Mitragotri S, Blankschtein D, & Langer R (2001) Theoretical description of transdermal transport of hydrophilic permeants: application to low-frequency sonophoresis. *J Pharm Sci* 90(5):545-568; Peck K D, Ghanem A H, & Higuchi W I (1994) Hindered diffusion of polar molecules through and effective pore radii estimates of intact and ethanol treated human epidermal membrane. *Pharm Res* 11(9):1306-1314.). Applications of these models to phage transport and their comparison with experimental observations are presented below.

Basics of these models have been published ((Tang H, Mitragotri S, Blankschtein D, & Langer R (2001) Theoretical description of transdermal transport of hydrophilic permeants: application to low-frequency sonophoresis. (Translated from eng) *J Pharm Sci* 90(5):545-568 (in eng); Peck K D, Ghanem A H, & Higuchi W I (1994) Hindered diffusion of polar molecules through and effective pore radii estimates of intact and ethanol treated human epidermal membrane. (Translated from eng) *Pharm Res* 11(9):1306-1314 (in eng)) and a summary of these models is provided below. These models have been applied to describe transport of large molecules such as dextran which has a hydrodynamic radius of 2.6 nm, which, though smaller than the radius of the phage (~4 nm), is of the same order of magnitude. The following analysis is based on extrapolation of these models and provides informative context for interpreting phage permeation through skin.

Polar Pathway:

Polar (or porous) pathways have been used to describe transdermal diffusion of several hydrophilic solutes including macromolecules (Tang H, Mitragotri S, Blankschtein D, & Langer R (2001) Theoretical description of transdermal transport of hydrophilic permeants: application to low-frequency sonophoresis. (Translated from eng) *J Pharm Sci* 90(5):545-568 (in eng); Mitragotri S, et al. (Mathematical models of skin permeability: An overview. (Translated from Eng) *Int J Pharm* (in Eng); Tezel A, Sens A, & Mitragotri S (2003) Description of transdermal transport of hydrophilic solutes during low-frequency sonophoresis based on a modified porous pathway model. (Translated from eng) *J Pharm Sci* 92(2):381-393 (in eng); Tezel A, Sens A, & Mitragotri S (2002) A theoretical analysis of low-frequency sonophoresis: dependence of transdermal transport pathways on frequency and energy density. (Translated from eng) *Pharm Res* 19(12): 1841-1846 (in eng); Tezel A & Mitragotri S (2003) On the origin of size-dependent tortuosity for permeation of hydrophilic solutes across the stratum corneum. (Translated from eng) *J Control Release* 86(1):183-186 (in eng); Polat B E, Seto J E, Blankschtein D, & Langer R (Application of the aqueous porous pathway model to quantify the effect of sodium lauryl sulfate on ultrasound-induced skin structural perturbation. (Translated from Eng) *J Pharm Sci* (in Eng); Seto J E, Polat B E, Lopez R F, Blankschtein D, & Langer R (Effects of ultrasound and sodium lauryl sulfate on the transdermal delivery of hydrophilic permeants: Comparative in vitro studies with full-thickness and split-thickness pig and human skin. (Translated from eng) *J Control Release* 145(1): 26-32 (in eng); Tang H, Blankschtein D, & Langer R (2002) Prediction of steady-state skin permeabilities of polar and nonpolar permeants across excised pig skin based on measurements of transient diffusion: characterization of hydration effects on the skin porous pathway. (Translated from eng) *J Pharm Sci* 91(8):1891-1907 (in eng); Tang H, Blankschtein D, & Langer R (2002) Effects of low-frequency ultrasound on the transdermal permeation of mannitol: comparative studies with in vivo and in vitro skin. (Translated from eng) *J Pharm Sci* 91(8):1776-1794 (in eng)).

In order to cross the stratum corneum (SC), hydrophilic solutes need to penetrate multiple lipid bilayers. However, given the low permeabilities of hydrophilic solutes across lipid bilayers, it appears unlikely that hydrophilic molecules can diffuse across the SC by the classical partition-diffusion process that plays an important role for hydrophobic solutes. Transdermal penetration of such solutes has been proposed to take place primarily through defects in the stratum corneum that exist in various physical form including grain boundaries, fault-dislocations, nanoscale pinholes or other abnormalities in skin structure. Hydration of the stratum corneum may further increase the occurrence of such defects. The precise size of these defects depends on the type of defect and may span a length scale of 1-100 nm.

A general expression for the permeability coefficient, $K_P^{pore}$, of a hydrophilic permeant diffusing through skin is given by the porous pathway as follows:

$$K_P^{pore} = \frac{\varepsilon D^\infty}{\tau L} \left( \int_0^\infty \gamma(r) H(\lambda) dr \right) \quad [1]$$

where $\varepsilon$, $\tau$, and L are the porosity, tortuosity and thickness of the membrane, respectively and $D^\infty$ is the solute diffusion coefficient in infinite dilution. $H(\lambda)$ is the steric hindrance factor, where $\lambda$ is the ratio of the hydrodynamic radius of the permeant, $r_h$, and the effective pore radius of the skin, r (that is, $\lambda = r_h/r$). The relationship between $H(\lambda)$ and $\lambda$ is given by the hindered transport theory and is described in the literature (11). $\gamma(r)$ is the pore size distribution in skin and it has been described for porcine skin by the following function (4).

$$\gamma(r) = 0.024 \exp(-0.00045 r^2) \quad [2]$$

To put Eq. [2] is perspective, consider the energetics of pore (or void) formation in a medium, for example skin. The probability of pore formation can be related to the free energy of pore formation according to the following general equation.

$$\text{probability} \propto \exp\left(-\frac{\pi r^2 E}{kT}\right) \quad [3]$$

where E is the free energy of pore formation per unit area per unit pore. A comparison of Eqs. [2] and [3] indicates that the value of E for a pore with a 4 nm radius in porcine skin is <1 kT, a value that is relatively small.

Values of $\epsilon$ for porcine skin have been determined to be about $2 \times 10^{-5}$ (4). Similarly, tortuosity, $\tau$, for diffusion of large hydrophilic solutes in porcine SC has been shown to be ~1 (4). $D_p^\infty$ is the solute diffusion coefficient in water and has been calculated using correlations such as the Wilke-Chang or Stoke-Einstein equation as follows.

$$D_p^\infty = \frac{2.6 \times 10^{-5}}{r_h} \quad [4]$$

where $r_h$ is in Å and $D_p^\infty$ is in cm$^2$/s. By combining Eqs. [1], [2] and [4], the contribution of porous pathways for a solute of radius $r_h$ can be estimated as follows.

$$K_P^{pore}(r_h) = \frac{1.3 \times 10^{-3}}{r_h} \int_{r_h}^{\infty} H(\lambda)\gamma(r)dr \quad [5]$$

where, $K_P^{pore}$ is in cm/hour. By substituting $r_h$=40 Å (corresponding to radius of phage), one gets $K_P^{pore}(r_h)$~$10^{-8}$ cm/hr.

Contribution of Appendages:

Large solutes may also be able to diffuse across the skin through appendages. While the density of hair follicles varies substantially with anatomical location, the average density of hair follicles in porcine skin is estimated to be approximately 10 per cm$^2$. A large fraction of the follicle, however, is occupied by the hair and is not available for transport. The contribution of shunts to skin permeability is given by the following.

$$K_P^{shunt} = \frac{\phi_s D_s}{L_{shunt}} \quad [6]$$

where, $\phi_s$ is the fraction of skin area occupied by follicles that is available for transport. $D_s$ is the solute diffusion coefficient in the contents within the follicles and $L_{shunt}$ is the diffusion path length through follicles. The area fraction of skin in the follicle that is available for transport is ~$10^{-4}$ cm$^2$/cm$^2$. $D_s$ can be estimated using the Wilke-Change Equation or the Stoke-Einstein relationship. Assuming the follicles are filled with a viscous liquid and given the large size of the phage, $D_s$ can be approximated to be ~$10^{-8}$ cm$^2$/s. $L_{shunt}$ is ~500 μm. By substituting the above values for $\phi_s$ and $L_{shunt}$ one can obtain the following expression for $K_P^{shunt}$ ~$10^{-7}$ cm/hr.

The above equations therefore estimate that phage permeability across porcine skin in the range of $10^{-7}$-$10^{-8}$ cm/hr.

To compare these estimates with experimental data, phage permeation across porcine skin was measured as described previously herein. Control phage (phage without any peptide displayed) exhibited a permeability ~$10^{-9}$ cm/hr. Phage that displays heptaglycine also exhibited a low permeability of ~$10^{-9}$ cm/hr. The entire phage display library exhibited a permeability of ~$10^{-8}$-$10^{-7}$ cm/hr and the permeability of phage displaying the SPACE sequence was $10^{-7}$-$10^{-6}$ cm/hr. These numbers are generally consistent with theoretical predictions. Note that the measured permeabilities may not represent steady-state values and may not fulfill the classical definition of permeability; nonetheless, these numbers provide reasonable values to allow comparisons with theoretical predictions.

Given that all phage particles used in this study were of identical size, the likely explanation for higher permeability of SPACE phage over control phage (no peptide displayed) is due to the peptide displayed on the surface of the phage. The porous pathway model assumes that partitioning of solutes in the skin is unity, that is, the solute exhibits no affinity towards the skin. If SPACE phage were to exhibit higher affinity towards the skin, it would lead to higher portioning and penetration of phage across the skin. Experimental observations indeed suggest that SPACE increases the affinity of the cargo towards skin components, especially keratin. Without intending to be bound by any particular theory, it is hypothesized that this increased affinity is the primary reason behind increased penetration of SPACE phage over control phage.

To further confirm this hypothesis, experiments were conducted where the effect of excess SPACE peptide on permeation of SPACE phage across porcine skin was assessed. Specifically, SPACE sequence-displaying phage was placed on the skin in presence of about a 100,000-fold excess SPACE peptide (~$10^5$ free SPACE peptides per SPACE peptide on phage). Excess SPACE peptide significantly reduced permeation of SPACE phage and the permeability of SPACE-phage phage in this case was close to heptaglycine phage (~$10^{-10}$ cm/hr).

Example 3

Dermis Screen

In a separate experiment, phage screening was performed to isolate phage that localized in the dermis. For the dermis screen, the phage display library was also placed in the donor compartment of the FDC. After 24 hours, the liquid from the donor compartment was removed and the skin was placed at 60° C. for 90 seconds. The epidermis was then removed from the dermis. To extract phage from the dermis, the dermis was cut up into small pieces and then homogenized (IKA disperser). The homogenate was spun down at 5,000 rpm for 5 minutes and then re-suspended in PBS and incubated at room temperature for 5 minutes. The samples were then centrifuged again and washed two more times. After the final centrifuge spin, the homogenates were re-suspended in 1% NP40 (Sigma) to elute the remaining phage from the dermis. The eluate was then plated and amplified according to the methods listed above. This was repeated for a total of 5 rounds. At the end of the fifth round of screening, about $1.9\times10^5$ phage were recovered from the dermis. Phage were sequenced and the three leading sequences in the fifth round were AC-KTG-SHNQ-CG (SEQ ID NO:15) (30%), AC-MGPSSML-CG (SEQ ID NO:16) (30%) and AC-TDPNQLQ-CG (SEQ ID NO:17) (20%). In view of the similarity between the AC- KTGSHNQ-CG (SEQ ID NO:15) peptide and the SPACE peptide identified above, the SPACE peptide was selected for further studies.

Example 4

Penetration of Fluorescently Labeled Phage

Phage clones displaying the SPACE peptide were fluorescently labeled and tested for their ability to penetrate into skin. Phage particles were labeled using the Alexa Fluor 488 protein labeling kit (Invitrogen). The Alexa Fluor 488 contains a TFP ester which reacts with the primary amine groups on the coat proteins of the phage. $2 \times 10^{12}$ pfu in DI water or PBS were added to DI water to obtain a total volume of 500 µL. The phage solution was then added to 50 µL of 1M sodium bicarbonate and the resulting solution was placed into a vial containing the fluorescent dye and was at room temperature for 1 hour. The phage were then purified with PEG/NaCl to remove the excess unreacted dye and titered.

Full thickness porcine skin was obtained from the lateral abdominal region of Yorkshire pigs. The skin was stored at −80° C. and defrosted immediately prior to use. The conductivity of the skin was measured to ensure the integrity of the skin barrier. Skin samples with a resistivity above 50 kΩ were used for experiments. Fluorescently labeled phage clones displaying the SPACE peptide or a scrambled peptide sequence (AC-THGQTQS-CG) (SEQ ID NO:25) were placed in the donor compartment of the FDC. To resemble the phage screening experiments, $2 \times 10^{11}$ pfu was added to the donor compartment and the skin samples were harvested after 24 hours. Skin samples were then prepared for imaging with confocal microscopy.

Preparation of Skin Samples for Confocal Microscopy Imaging

The skin samples were placed into 4% paraformaldehyde (Electron Microscopy Sciences) overnight at 4° C. immediately after being harvested and rinsed with DI water. Skin samples were then frozen in O.C.T. Compound and sectioned at a thickness of 20 µm on a cyrotome (Leica). The tissues were mounted on slides which were positively charged to adhere the tissue to the glass slide Fisher Scientific). The slides were washed in DI water for 5 minutes prior to staining with 5 µg/mL Hoechest 33342 (Invitrogen) for 5 minutes. The slides were then washed again in DI water for 5 minutes and then allowed to dry completely at room temperature in the dark. 10 µL of Permount mounting medium (Fisher Scientific) was placed on top of the skin section along with a glass cover slip and then the slides were sealed. All samples were imaged on a confocal microscope (Leica and Olympus Fluoview 500).

Figure 2:
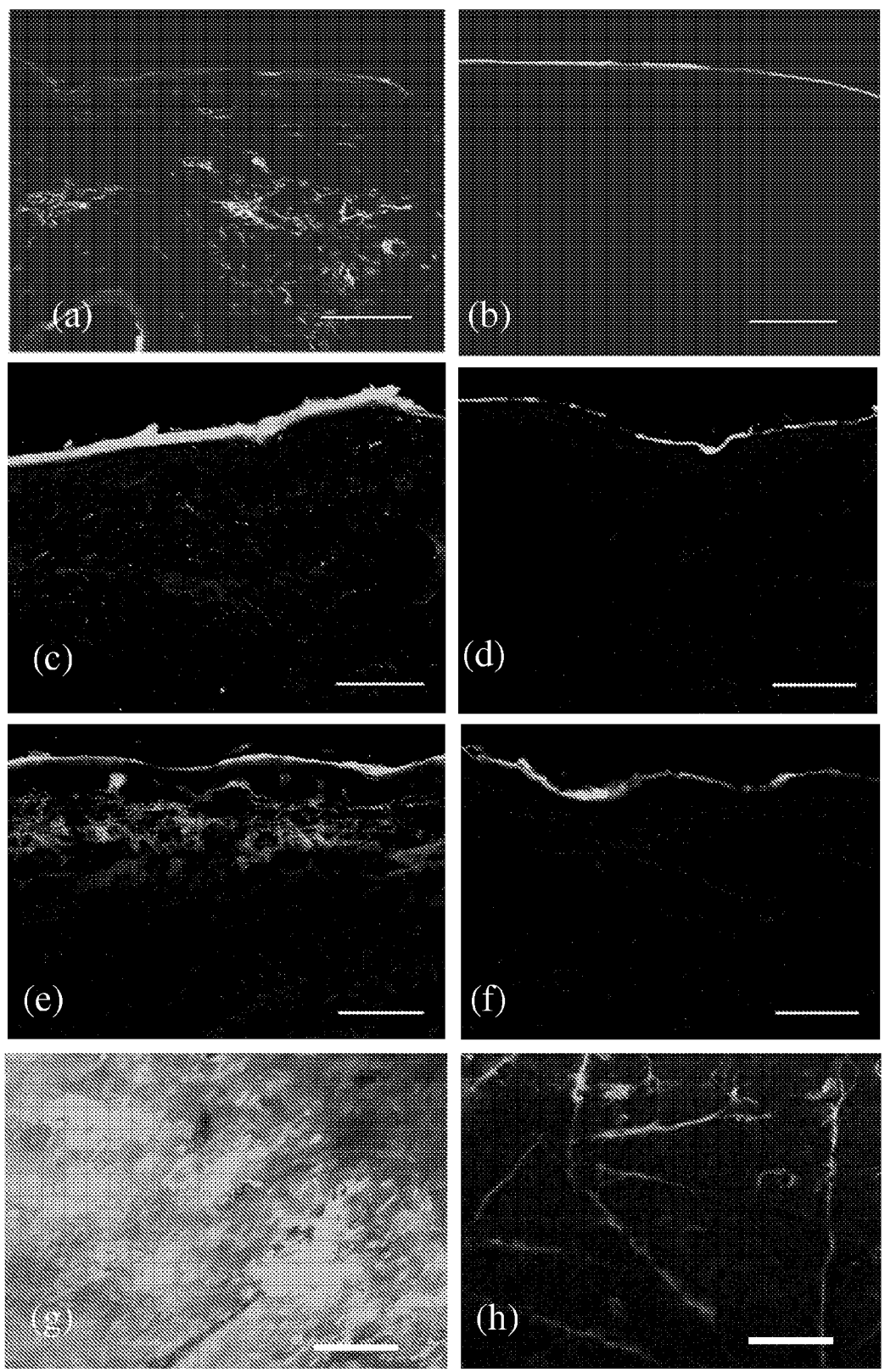
FIG. 2 shows confocal microcopy images depicting penetration of fluorescently labeled molecules through skin. (a,b) Penetration of fluorescently labeled phage displaying peptides into porcine skin. (c,d) Penetration of biotinylated peptide-streptavidin coated quantum dots into porcine skin. (e,f) Penetration of fluorescently labeled peptide into human skin. (g,h) Top view (looking down on SC) of fluorescently labeled peptide in human skin. (a,c,e,g) represent images of SPACE peptide and (b,d,f,h) represent images of control peptide. Scale bar=200 µm.

The imaging results for the above experiment are shown in FIG. 2, panels (a) and (b). Fluorescently labeled phage clones displaying SPACE peptide exhibited small but detectable penetration into skin (a). In contrast the scrambled control peptide sequence (AC-THGQTQS-CG) (SEQ ID NO:25) exhibited only superficial penetration (b).

Example 5

Peptide Penetration into Porcine Skin

The ability of the SPACE peptide to penetrate porcine skin when removed from phage was tested as follows. Full thickness porcine skin was obtained and prepared as described above. Fluorescently labeled peptides, 200 µL of a 1 mg/mL solution, were placed in the donor compartment of the FDC. After 24 hours, the remaining solution in the donor compartment was removed and the FDC was dismantled. The skin sample was retrieved and rinsed with DI water to remove excess peptide or peptide complex on the surface of the skin. Skin samples were then prepared for imaging with confocal microscopy as described above.

The imaging results for the above experiment are shown in FIG. 1, panels (c) and (d). The SPACE peptide, when removed from the phage, penetrated into the skin (c). Consistent with the observations made with the entire phage, SPACE peptide was found to localize strongly in the dermis. No significant penetration of the control peptide was observed (d).

Example 6

Peptide and Macromolecule Penetration in Porcine Skin

The ability of the SPACE peptide to carry macromolecular cargos across the SC was tested as follows. Full thickness porcine skin was obtained and prepared as described above. The peptide was first conjugated to the macromolecule as described in greater detail below and then the peptide-macromolecule complex was placed into the donor compartment of the FDC. After 24 hours, the remaining solution in the donor compartment was removed and the FDC was dismantled. The skin sample was retrieved and rinsed with DI water to remove excess peptide complex on the surface of the skin. Skin samples were then prepared for imaging with confocal microscopy as described above.

To conjugate the peptide to the macromolecule streptavidin, 80 µL of a 1 mg/mL biotinylated peptide solution was incubated with 20 µL of a 2 mg/mL streptavidin-Alexa Fluor 488 conjugate (Invitrogen) solution and incubated at room temperature for 30 minutes. The resulting solution was then placed into the donor compartment of the FDC. Skin samples were harvested after 24 hours and imaged as described above.

Streptavidin, when conjugated to biotinylated SPACE peptide, permeated well beyond the SC and some localization of streptavidin was found in the epidermis and dermis (FIG. 1, panel (e)). Streptavidin not conjugated to SPACE peptide exhibited minimal penetration into epidermis (FIG. 1, panel (f)).

The ability of the SPACE peptide to carry quantum dots across the SC was also tested. For the delivery of quantum dots into the skin, 198 µL of a 100 ng/mL biotinylated peptide solution was incubated with 200 µL of QDot 525 streptavidin conjugate (Invitrogen) for 1 hour at room temperature. The 200 µL suspension was then placed into the donor compartment of the FDC. Skin samples were harvested after 24 hours and confocal microscopy imaging was as described above.

SPACE peptide, when conjugated to streptavidin-coated quantum dots, led to a detectable but smaller amount of transport. No significant penetration of quantum dots conjugated to control peptide was observed. See, FIG. 2, panels (c) and (d) respectively. Without intending to be bound by any particular theory, the reduced amount of transport may be due to the relatively large size of the quantum dots.

Example 7

Peptide Penetration in Human Skin

The ability of the SPACE peptide to penetrate human skin when removed from phage and conjugated to an exemplary small molecule in the form of a fluorescent tag was tested as follows. Full thickness human skin was obtained from the National Disease Research Interchange. The skin was stored at −80° C. and defrosted immediately prior to use. The conductivity of the skin was measured to ensure the integrity of the skin barrier. Skin samples with a resistivity above 50 kΩ were used for experiments. Fluorescently labeled peptides, 200 μL of a 1 mg/mL solution, were placed in the donor compartment of the FDC. After 24 hours, the remaining solution in the donor compartment was removed and the FDC was dismantled. The skin sample was retrieved and rinsed with DI water to remove excess peptide or peptide complex on the surface of the skin. Skin samples were then prepared for imaging with confocal microscopy as discussed above.

SPACE peptide was shown to successfully cross human skin and exhibited penetration similar to that found in porcine skin. See, FIG. 2, panels (e) (SPACE) and (f) (control). When observed from the top, high localization of the SPACE peptide within the corneocytes was found whereas no significant penetration of the control peptide was observed. See, FIG. 2, panels (g) and (h) respectively.

Example 8

Peptide Penetration into Mouse Skin In-Vivo

The ability of the SPACE peptide to penetrate mouse skin in-vivo was tested as follows. 200 μl of fluorescently labeled peptide (1 mg/ml) was applied on the skin of a mouse. Penetration was assessed at various time points by harvesting the skin, sectioning it and observing under a microscope.

Figure 3:
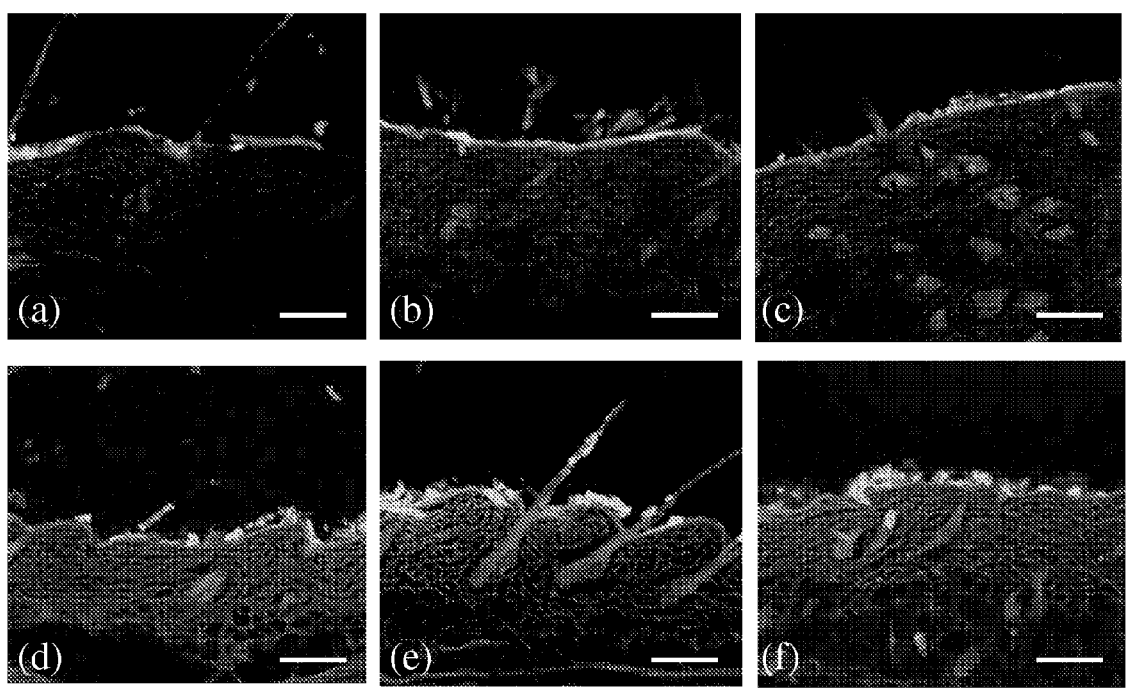
FIG. 3 shows images of the penetration of fluorescently labeled peptide into mouse skin in vivo after 30 minutes. Three representative images are provided for each case. (a-c) Penetration of fluorescently labeled control peptide and (d-f) fluorescently SPACE peptide. Scale bar=50 µm.
Figure 4:
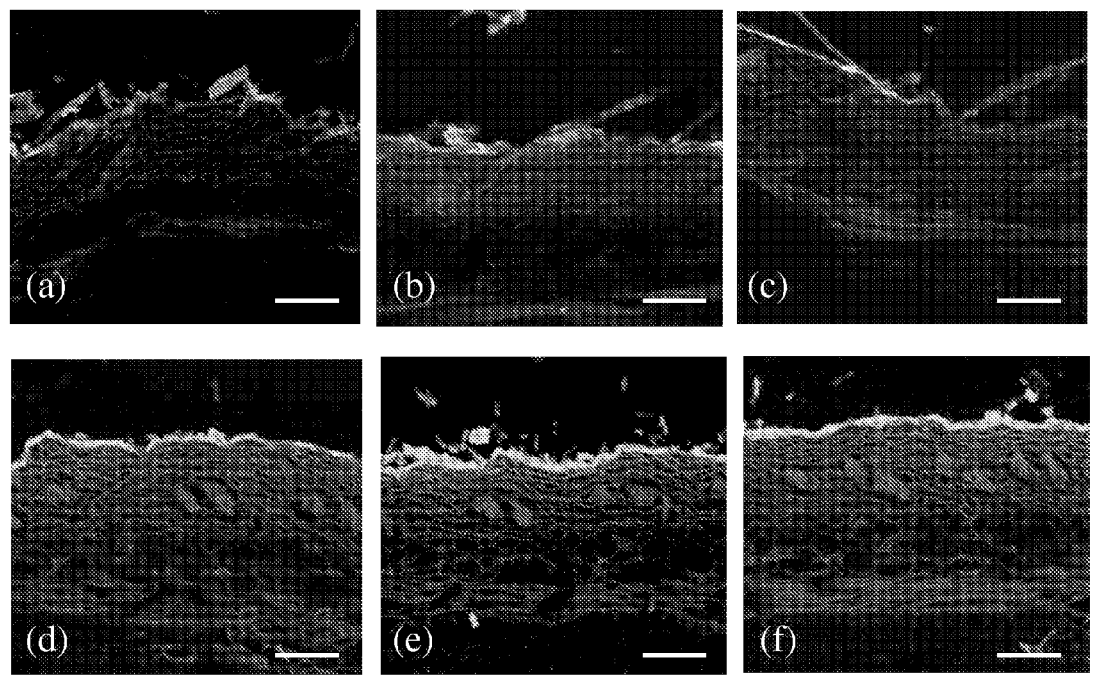
FIG. 4 shows images of the penetration of fluorescently labeled peptide into mouse skin in vivo after 2 hours. Three representative images are provided for each case. (a-c) Penetration of fluorescently labeled control peptide and (d-f) fluorescently labeled SPACE peptide. Scale bar=50 µm.

SPACE peptide penetrated into mouse skin in vivo at levels significantly higher than control peptide (FIG. 3, panels (a)-(f), and FIG. 4, panels (a)-(f)). Application of the SPACE peptide on mouse skin for 30 minutes (FIG. 3) resulted in penetration and application for two hours (FIG. 4) resulted in significant penetration into the skin and localization in the deep dermis, consistent with that seen in porcine and human skin.

Example 9

Stratum Corneum Studies

In order to further characterize the ability of the SPACE peptide to penetrate the SC. Experiments were conducted using isolated SC as follows. To isolate the SC from full thickness skin, the skin was placed in a 60° C. water bath for 90 seconds. After removal from the water bath, the epidermis was separated from the dermis. The SC was then placed epidermis side down in a petri dish containing 0.25% trpysin to remove the epidermis from the SC. The SC was washed in DI water and then allowed to dry completely at room temperature. To delipidize the SC, the SC was placed in the following chloroform:methanol solvent mixtures: 2:1 (v/v), 1:1 (v/v), and 1:2 (v/v) for 15 minutes each. To confirm the removal of lipids, FTIR was performed on the SC samples before and after exposure to the solvent mixtures.

Fourier Transform Infrared (FTIR) Spectroscopy of SC

FTIR was performed on SC samples to see the effects different peptide solutions had on the SC structure. SC was cut into 1.5×1.5 cm pieces and a control spectrum was obtained for each piece prior to exposure with peptide. 2 mL of a peptide solution was then incubated with the SC for 24 hours. The SC samples were then rinsed with DI water and allowed to completely dry at room temperature. The spectra were read again for each SC sample and the before and after spectra were compared to determine the effect each peptide had on SC structure. Spectra were obtained using a Nicolet Magna 850 spectrometer with a resolution of 2 cm$^{-1}$ and averaged over 400 scans.

Figure 5:
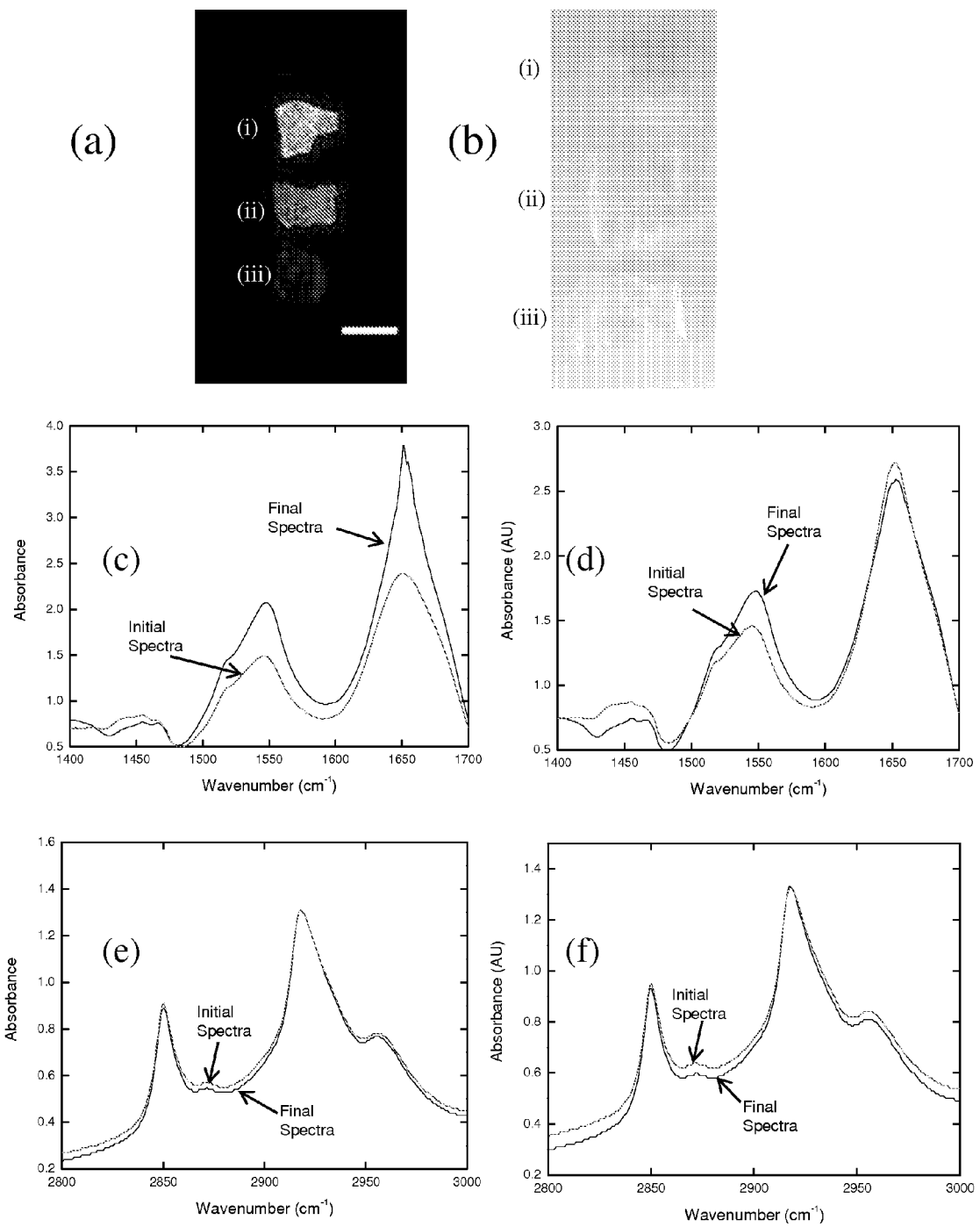
FIG. 5 shows image results for the binding of fluorescently labeled peptide to delipidized stratum corneum (a,b) and FTIR spectra of stratum corneum before and after treatment with peptide (c-f). Images of delipidized SC under UV (a) and visible light (different samples) (b). (i, ii, iii) represent the SPACE peptide, control peptide and no peptide respectively. Scale bar=1 cm. Note that the stratum corneum samples shown above were delipidized to ensure a comparison of binding ability and not transport ability of the peptides. Hence, the difference between the control and SPACE peptide as seen above may not directly translate to their effect on skin penetration. (c,d) 1400-1700 $cm^{-1}$ region of spectra for the SPACE peptide and control peptide respectively. (e,f) 2800-3000 $cm^{-1}$ region of the spectra for the SPACE peptide and control peptide respectively. Initial and final spectra indicated by arrows.
Figure 6:
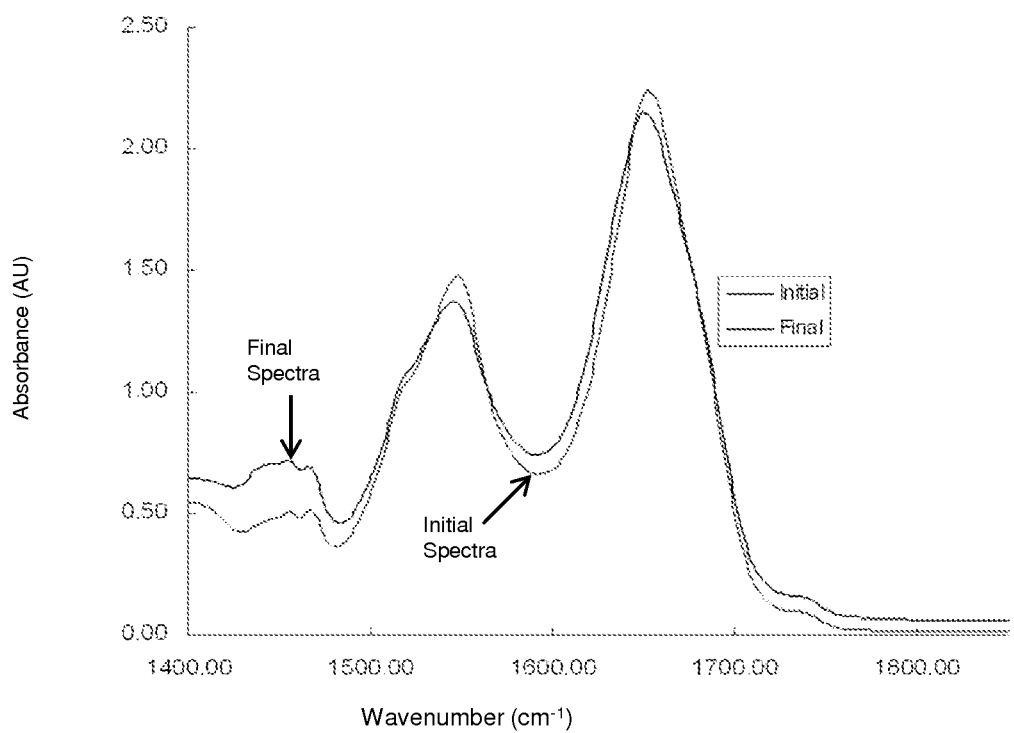
FIG. 6 provides FTIR spectra of amide I and amide II region for stratum corneum before and after treatment with no peptide.
Figure 7:
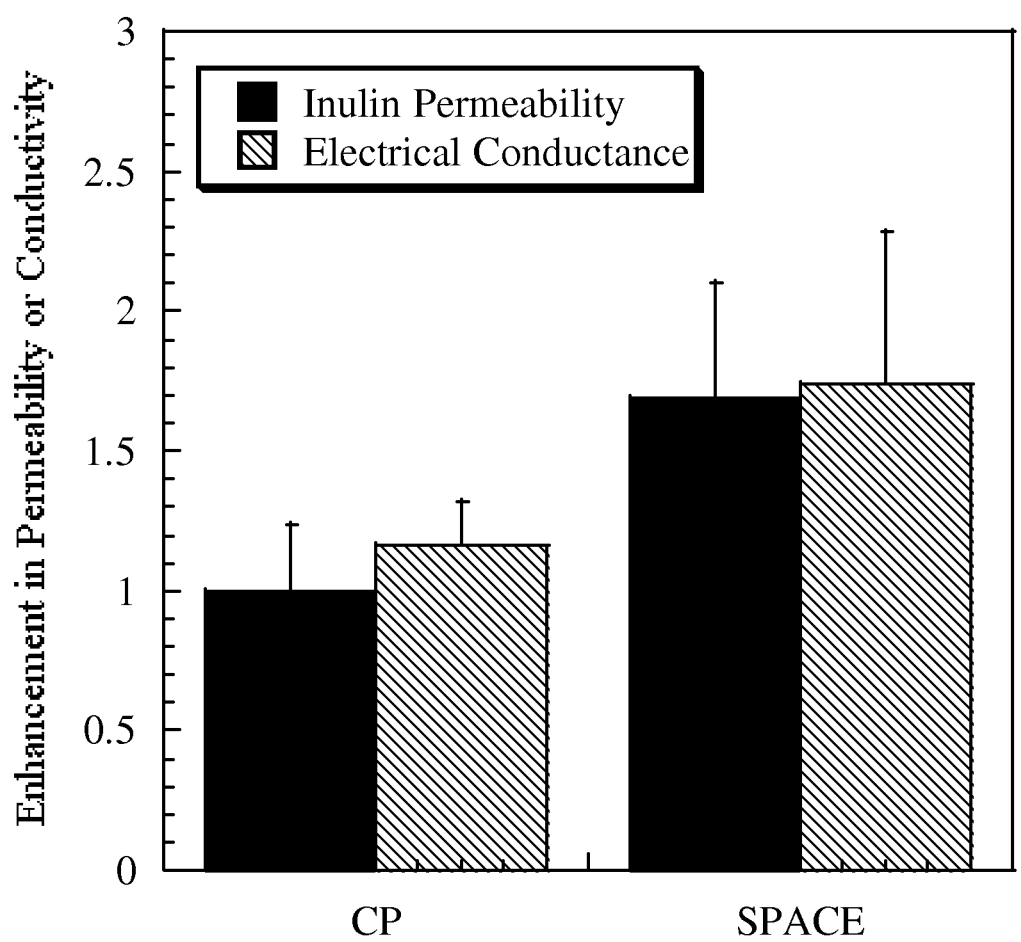
FIG. 7 shows graphical results for inulin permeability and the electrical conductivity enhancement of porcine skin after co-incubation with control (CP) and SPACE peptide.

The experiments with isolated human SC revealed that the SPACE peptide binds to corneocyte proteins, most likely to keratin (FIG. 5, panels (a) and (b)). Fourier Transform Infrared Spectroscopy (FTIR) studies also confirmed the effect of SPACE peptide on keratin. Specifically, SC exposed to SPACE peptide exhibited changes in the FTIR spectrum, indicative of structural changes in keratin (FIG. 5, panel (c)). The control peptide had no significant effect on protein structure in FTIR compared to that seen in the absence of any peptide (FIG. 5 panel (d) and FIG. 6). FTIR also showed that the SPACE peptide had no detectable effect on SC lipids (FIG. 5, panels (e) and (f)). Neither a change in the area of the symmetric $CH_2$ stretching peak nor a shift in center frequency was found indicating that the SPACE peptide did not induce extraction or fluidization of SC lipid. Consistent with the FTIR data, exposure to SPACE peptide did not induce a significant change in skin's electrical conductivity (FIG. 7). Specifically, the electrical conductivity of skin increased by about 1.7 (+/−0.6)-fold after 24 hour incubation with the SPACE peptide. This enhancement, though higher than that observed for the control peptide, was relatively modest. Similarly, co-incubation of SPACE peptide with inulin, a large hydrophilic molecule led to only a modest increase in its permeability (FIG. 7), indicating that the SPACE peptide is primarily effective in enhancing permeation of conjugated but not co-administered cargos.

Without intending to be bound by any particular theory, the primary effect of SPACE peptide may be to enhance partitioning into the SC, primarily corneocytes, which subsequently enhances the ability of SPACE peptides and conjugates to cross the skin barrier. An additional effect of the peptide on penetration may also be potentially expected due to its ability to impact keratin structure.

Example 10

Penetration of SPACE Peptide into Viable Cells

Having confirmed the ability of the SPACE peptide to penetrate the SC, its ability to penetrate into viable cells including keratinocytes, fibroblasts, and endothelial cells (HUVECs) in cell cultures was tested.

For cell penetration studies, $1.2 \times 10^4$ cells were seeded on poly-d-lysine-coated glass bottom culture dishes (MatTek). For HUVEC cells, the culture dishes were coated with 1% gelatin prior to seeding with cells. After incubation at 37° C. for 4 hours, the media was removed and 20 μL of a 1 mg/mL fluorescent peptide solution was added to 180 μL of media and subsequently added to the cell culture dish. For the control, an equivalent amount of PBS was added in place of a peptide solution. After addition of the peptide, cell cultures were incubated at the appropriate condition for studying cellular penetration (4° C. or 37° C.) and incubated for either 6 or 24 hours. Cells were prepared for imaging with confocal microscopy.

Cell Culturing Conditions

Human adult epidermal keratinocytes (Invitrogen) were cultured in EpiLife Medium (Invitrogen) supplemented with Human Keratinocyte Growth Supplement (Invitrogen), human skin fibroblasts (ATCC) were cultured in Dulbecco's Modified Eagle's Medium (ATCC) supplemented with 10% fetal bovine serum, pooled human umbilical vein endothelial cells (HUVEC, Lonza) were cultured in M199 medium on 1% gelatin-coated flasks supplemented with 15% fetal bovine serum, 15 µg/mL endothelial cell growth supplement, 100 µg/mL heparin, and 2 mM L-glutamine, and MDA-MB-231 breast cancer cells were cultured in Dulbecco's Modified Eagle's Medium (ATCC) supplemented with 10% fetal bovine serum. All cell culture media were supplemented with 100 U/mL pencillin and 100 µg/mL streptomycin and cultures were grown under standard cell culture conditions (37° C. with 5% $CO_2$).

Preparation of Cell Culture Samples for Confocal Microscopy Imaging

After incubation, cells were washed with Hank's Balanced Salt Solution (HBSS, Lonza) and incubated with 1% trypan blue for 5 minutes to quench any fluorescence on the surface of the cell. The cells were then fixed with 4% paraformaldehyde for 3 minutes and again washed in HBSS. The cells were then incubated with Hoechest 33342 (5 µg/mL) for 5 minutes and then washed in HBSS. The cell culture dishes were then filled with HBSS and imaged using confocal microscopy (Olympus Fluoview 500).

Figure 8:
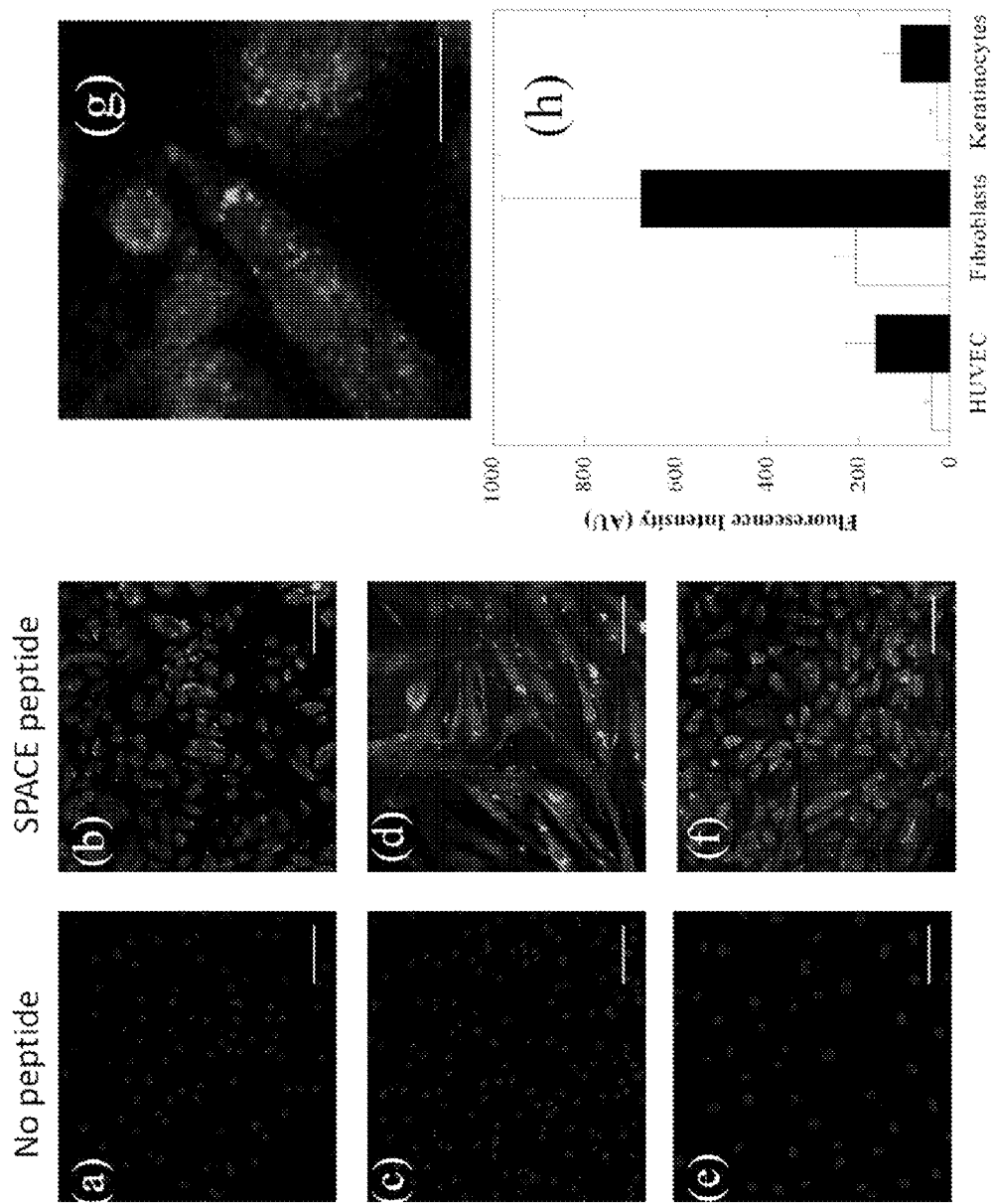
FIG. 8 shows the cellular penetration of SPACE peptide into various cell lines. (a,c,e) Confocal images of cells treated with no peptide (b,d,f) and cells incubated with fluorescently labeled SPACE peptide for 24 hours. (a,b) Human keratinocytes, (c,d) Human fibroblasts, and (e,f) Human Umbilical Vein Endothelial Cells (HUVEC). (g) Magnified image of SPACE peptide internalization in human keratinocytes. (h) Average fluorescence intensity of control peptide (open bars) and SPACE peptide (closed bars) internalization after 24 hours in HUVEC, fibroblasts and keratinocytes. Error bars indicate SD (N> or =30). Scale bar=100 µm (a-f) and 20 µm (g).
Figure 9:
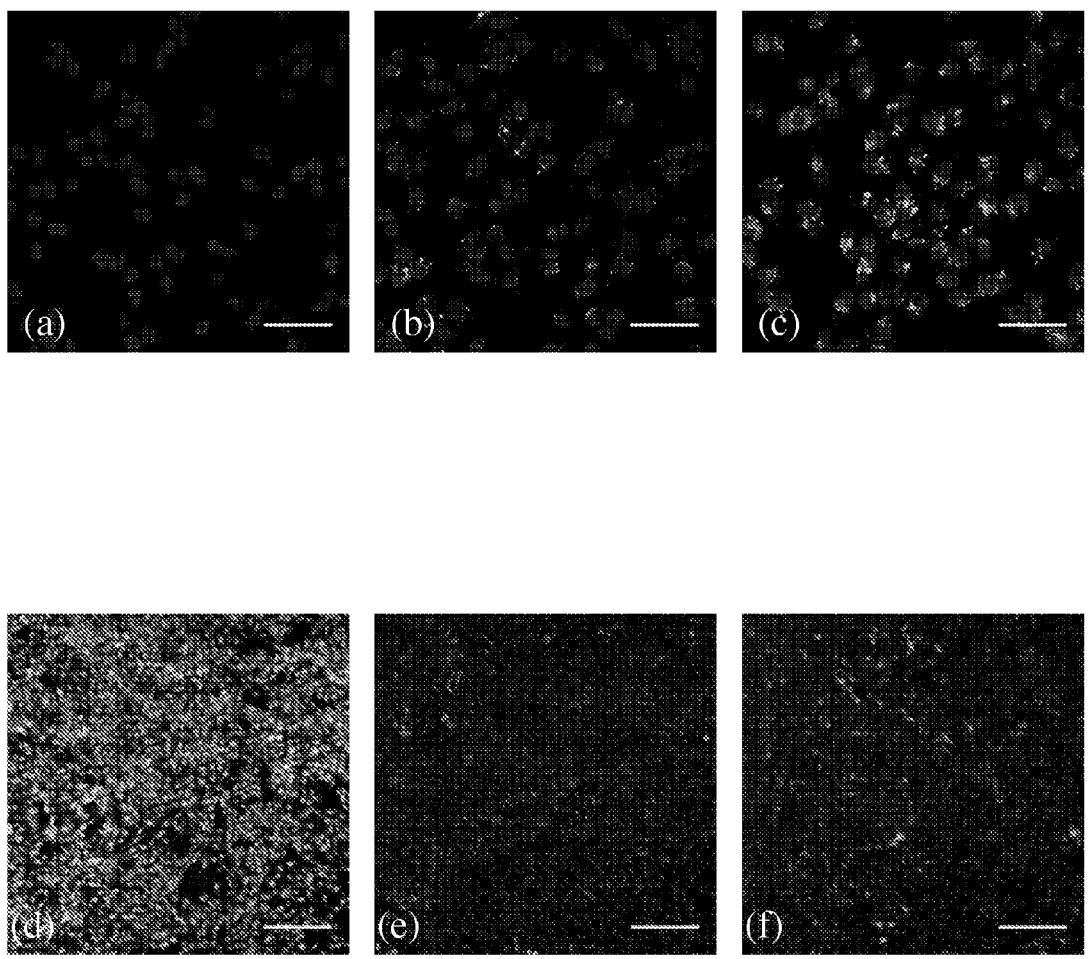
FIG. 9 shows image results for the Penetration of fluorescently labeled peptide into MDA-MBA-231 human breast cancer cells after 6 hours (a-c). Images of cells with no peptide (a), control peptide (b), and SPACE peptide (c). Scale bar=50 µm, FIG. 7 also shows confocal images of GFP-expressing endothelial cells after treatment with GFP siRNA complexed with Lipofectamine (d-f). (d) Treatment of cells with Lipofectamine only (no siRNA), (e) with Lipofectamine complexed with GFP siRNA, and (f) with Lipofectamine complexed with SPACE-GFP siRNA. Scale bar=200 µm.

Significant penetration of SPACE peptide was demonstrated for all cell lines (FIG. 8, panels (a)-(f), FIG. 8, panel (g) shows a magnified view of SPACE peptide internalization in keratinocytes). In all cases, the extent of internalization of SPACE peptide was higher than that of control peptide indicating that cellular penetration occurred in a sequence-specific manner (FIG. 8, panel (h)). SPACE peptide also exhibited internalization in breast cancer cells (MD-MB-23, FIG. 9, panels (a)-(c)). The ability to penetrate all tested types of cells suggest that the mode of entry into cells for SPACE is through a pathway that is common to all studied cell lines and not due to a particular membrane protein unique to keratinocytes.

Example 11

Cell Penetration Mechanism Studies

Figure 10:
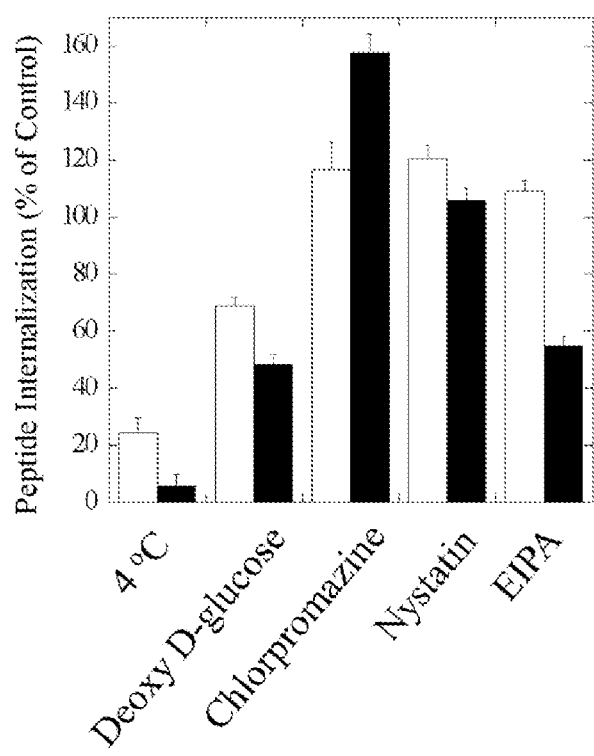
FIG. 10 shows the results for cellular mechanism and toxicity studies. (a) Peptide internalization (percent of control) for control peptide and SPACE peptide at 4° C. and with the endocytosis inhibitors deoxy-D-glucose, chlorpromazine, nystatin, and EIPA in human keratinocytes. (b) Cell proliferation of human keratinocytes in the presence of control peptide (open bars) or SPACE peptide (closed bars) at 0.1 mg/mL and 1.0 mg/mL. Error cars indicate SD (N=4).
Figure 10:
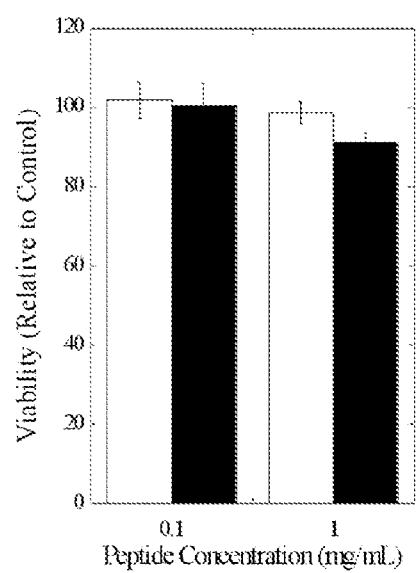

To determine the potential mechanism of cellular penetration for SPACE peptide, the effect of several endocytosis inhibitors including incubation at 4° C. on internalization was tested in human keratinocytes (See, FIG. 10, panel (a)).

Endocytosis Inhibitors

For cell mechanism studies, cells were incubated with various endocytosis inhibitors or at 4° C. for 1 hour prior to the addition of fluorescently labeled peptides. The endocytosis inhibitors used were EIPA (Invitrogen) and chlorpromazine, nystatin, and deoxy-D-glucose (Sigma). EIPA was dissolved in DMSO and used at a concentration of 100 µM. Chlorpromazine, nystatin, and deoxy-D-glucose were dissolved in sterile water and used at the concentrations of 10 µg/mL, 25 µg/mL, and 5 mM respectively. Cells were incubated with fluorescently labeled peptide for 3 hours and then harvested for analysis using flow cytometry.

Preparation of Samples for Flow Cytometry

After incubation with fluorescently labeled peptide, the media was removed and cells were washed 3 times for 5 minutes each in HBSS to remove residual fluorescence. 0.25% trypsin (HyClone) was used to remove the cells from the cell culture plate. The cells were then centrifuged at 5,000 rpm for 5 minutes to pellet the cells. The cell pellet was resuspended in PBS, pH 7.4 on ice and samples were analyzed using the FACS Aria flow cytometer.

Incubation at 4° C. significantly reduced internalization of SPACE peptide (about 5% uptake compared to that at 37° C.) as well as the control peptide indicating that both enter cells through an active mechanism (FIG. 10, panel (a)). This was further confirmed by the use of deoxy-D-glucose which also resulted in the reduction of internalization of both peptides (~52%) (FIG. 10, panel (a)). To further assess the nature of the active uptake, cells were incubated with the clathrin-mediated endocytosis inhibitor chlorpromazine and the caveolae-mediated endocytosis inhibitor nystatin. Neither of them reduced the cellular internalization of SPACE peptide or the control peptide (FIG. 10, panel (a)). Finally, the effect of a macropinocytosis inhibitor 5-(N-ethyl-N-isopropyl) amiloride, EIPA, was tested. Exposure of cells to EIPA resulted in approximately 50% reduction in SPACE internalization (FIG. 10, panel (a)). In contrast, EIPA had no effect on control peptide internalization. Collectively, these results suggest that macropinocytosis plays a major role in the internalization of SPACE peptide, a conclusion that is shared by other cell penetrating peptides in the literature (Nakase I, et al. (2004) Cellular uptake of arginine-rich peptides: roles for macropinocytosis and actin rearrangement. *Mol Ther* 10(6): 1011-1022., Patel L N, Zaro J L, & Shen W C (2007) Cell penetrating peptides: intracellular pathways and pharmaceutical perspectives. *Pharm Res* 24(11):1977-1992.). Studies have reported that cargoes that are internalized by macropinocytosis are often not co-localized with endo/lysosomes implying that their entry into degrading lysosomal compartment can be potentially avoided (Tamaru M, Akita H, Fujiwara T, Kajimoto K, & Harashima H (2010) Leptin-derived peptide, a targeting ligand for mouse brain-derived endothelial cells via macropinocytosis. *Biochem Biophys Res Commun* 394(3):587-592, Walsh M, et al. (2006) Evaluation of cellular uptake and gene transfer efficiency of pegylated poly-L-lysine compacted DNA: implications for cancer gene therapy. *Mol Pharm* 3(6):644-653.). MTT assays on keratinocyte cultures revealed that the SPACE peptide was not toxic to cells at the concentration range studied here (0.1-1.0 mg/mL, FIG. 10, panel (b)).

Example 12

GFP Knockdown Using SPACE Peptide-Conjugated siRNA

The ability of SPACE peptide to penetrate into a variety of cells makes it an excellent candidate for siRNA delivery. This possibility was explored using green fluorescent protein (GFP)-expressing endothelial cells as a model cell line in vitro.

GFP-expressing endothelial cells (ATCC) were grown in Dulbecco's Modified Eagle's Medium supplemented with 10% fetal bovine serum. GFP siRNA, 5'-GAC GUA AAC GGC CAC AAG UUC N6-3' (SEQ ID NO:26) (Dharmacon), was conjugated to fluorescently labeled peptide (containing a free carboxyl group) through EDC chemistry.

A 10 mM peptide solution was incubated with a 10 mM solution of N-(3-Dimethylaminopropyl)-N'-ethylcarbodiimide hydrochloride (EDAC, Sigma) and a 9.5 mM solution of N-Hydroxysulfosuccinimide sodium salt (NHS, Sigma) in equal parts in MES buffer (pH 5.5) for 15 minutes. The amine modified siRNA was then added to the mixture to conjugate the peptide to siRNA and allowed to mix overnight.

The peptide-siRNA complex was added to the appropriate cell culture media to obtain a final concentration of 1 µM siRNA. The media along with peptide-siRNA was then added to the cells and allowed to incubate for 48 hours. Cells were imaged using confocal microscopy and image analysis was performed using ImageJ to determine the overall fluorescence intensity for each cell. Knockdown was determined as the percent of cells in the test case that possess intensity at least 30% lower than the mean intensity observed for the population in control case (no treatment).

Figure 11:
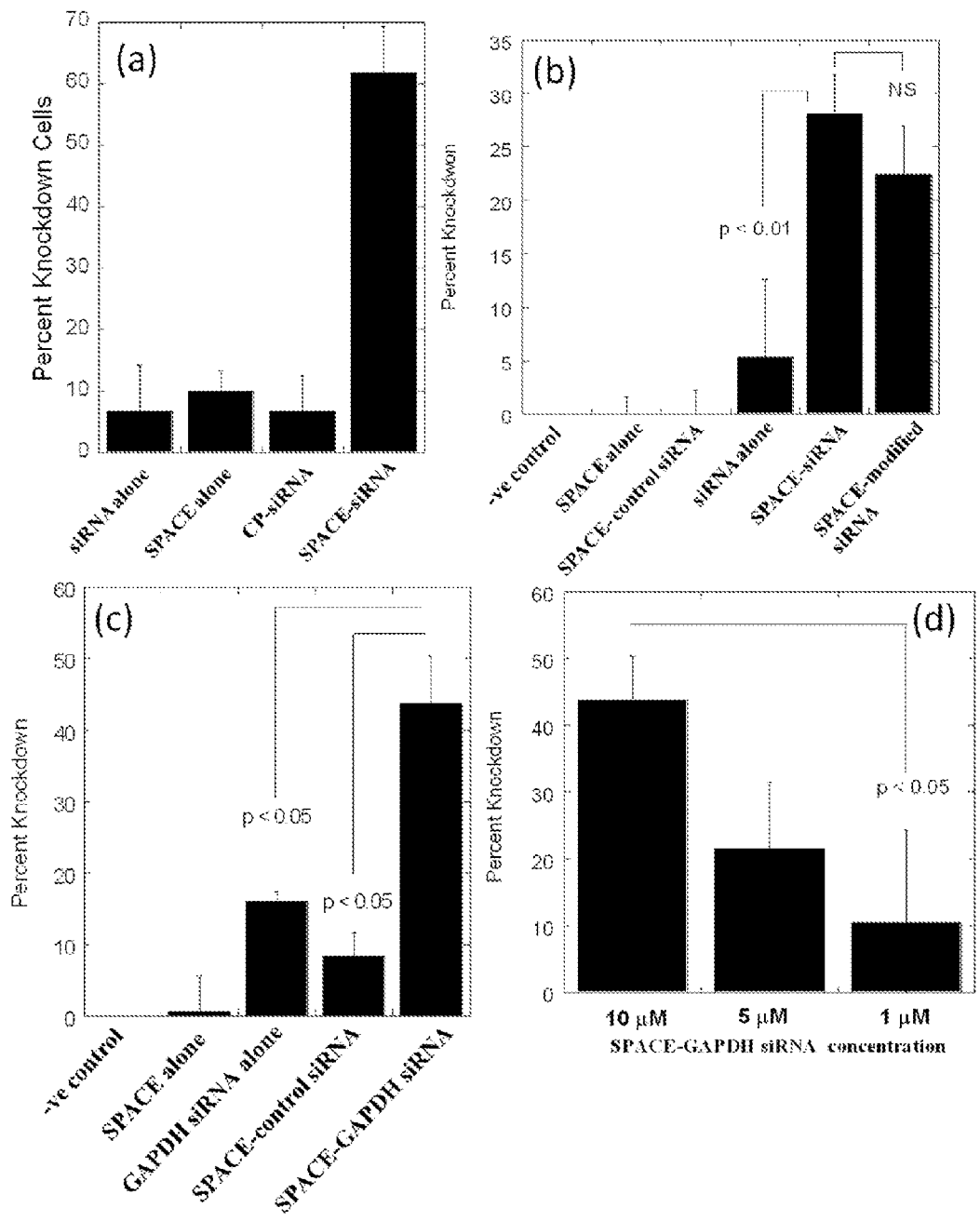
FIG. 11 shows the results for delivery of siRNA using the SPACE peptide. (a) Percentage knockdown of GPF in GFP-expressing endothelial cells. Error bars indicate SD (N> or =30), (b) Percentage knockdown of IL-10 protein levels in mice 24 hours after treatment. Error bars indicate SE (N> or =3), NS—not significantly different (p>0.15), (c) Percentage knockdown of GAPDH protein levels in mice 72 hours after treatment. Error bars indicate SE (N> or =3), (d) Dose dependence of GAPDH knockdown upon topical siRNA application. Error bars indicate SE (N> or =3).

SPACE peptide-conjugated siRNA induced significant knockdown of GFP (FIG. 11, panel (a)). In contrast, no significant knockdown was observed with siRNA alone, SPACE alone, SPACE conjugated to a control siRNA, or control peptide conjugated to siRNA. To determine whether siRNA conjugation to SPACE peptide had an adverse effect on the potency of siRNA, both unconjugated siRNA and SPACE-siRNA were complexed with Lipofectmine™ and knockdown was assessed. In both cases, knockdown was significant compared to control, that is, no siRNA treatment (FIG. 9, panels (d)-(f)).

Example 13

Dermal Penetration Using Peptide-Conjugated IL-10 siRNA In-Vivo

The ability of SPACE peptide to enhance dermal penetration of IL-10 siRNA was assessed as follows. This siRNA was selected due to its potential for treating atopic dermatitis, a major dermatological disease. Due to the insignificant knockdown seen with control peptide and the lack of skin penetration in vivo when compared to SPACE peptide, the control peptide was not assessed in the in vivo siRNA studies.

The siRNA sequences used in the in vivo studies are the following: IL-10: 5'-GAA UGA AUU UGA CAU CUU CUU N6-3' (SEQ ID NO:27), and luciferase (control): 5'-UAA GGC UAU GAA GAG AUA CUU N6-3' (SEQ ID NO:28). The 2-O-methyl modification was placed on all bases for IL-10. All siRNAs were purchased from Dharmacon.

siRNA delivery was performed in female Balb/C mice (Charles River Laboratories) between 6-8 weeks old according to protocols approved by the Institutional Animal Care and Use Committee. Mice were placed under anesthesia (1-2% isofluorane) and the hair on their back was lightly shaved. 200 µL of a 10 µM of peptide-siRNA solution or corresponding controls were topically applied over a 3 $cm^2$ area on the back of the animal. The solution was then covered with sterile gauze and a breathable bandage. After 24 hours, the mice were euthanized using $CO_2$ and skin samples were immediately taken using a 4 mm biopsy punch. Two 4 mm biopsies were randomly taken from the treatment area and immediately frozen in liquid nitrogen. The skin was then placed in a surfactant combination of 0.5% (w/v) 3-(Decyl dimethyl ammonio) propane sulfonate (DPS) and Brij 30 and homogenized (IKA disperser) on ice for 1 minute to extract the proteins from the skin samples. The homogenate was then centrifuged at 10,000 rpm for 5 minutes and the supernatant was collected. The total protein concentration was determined using the Micro BCA Protein Assay Kit (Pierce), IL-10 levels were determined using a mouse IL-10 ELISA (Raybiotech).

Application of IL-10 siRNA alone without the peptide produced no significant effect on IL-10 levels compared to mice that received no treatment, SPACE peptide alone, or SPACE conjugated to luciferase siRNA (control siRNA). In contrast, animals treated with SPACE conjugated to IL-10 siRNA and SPACE conjugated to 2-O-methyl modified IL-10 siRNA showed significant reduction in IL-10 levels (FIG. 11, panel (b)).

Example 14

Dermal Penetration Using Peptide-Conjugated GAPDH siRNA In-Vivo

As another example, SPACE peptide was conjugated to glyceraldehyde 3-phosphate dehydrogenase (GAPDH) siRNA and its effect on skin GAPDH levels was assessed as follows. This target was chosen since GAPDH is a common housekeeping protein and provides an example of a common siRNA target.

The siRNA sequences used in the in vivo studies are the following: GAPDH: 5'-GUG UGA ACC ACG AGA AAU AUU N6-3' (SEQ ID NO:29), and luciferase (control): 5'-UAA GGC UAU GAA GAG AUA CUU N6-3' (SEQ ID NO:28). All siRNAs were purchased from Dharmacon.

siRNA delivery was performed in female Balb/C mice (Charles River Laboratories) between 6-8 weeks old according to protocols approved by the Institutional Animal Care and Use Committee. Mice were placed under anesthesia (1-2% isofluorane) and the hair on their back was lightly shaved. 200 µL of a 10 µM of peptide-siRNA solution or corresponding controls were topically applied over a 3 $cm^2$ area on the back of the animal. The solution was then covered with sterile gauze and a breathable bandage. After 72 hours for, the mice were euthanized using $CO_2$ and skin samples were immediately taken using a 4 mm biopsy punch. Two 4 mm biopsies were randomly taken from the treatment area and immediately frozen in liquid nitrogen. The skin was then placed in a surfactant combination of 0.5% (w/v) 3-(Decyl dimethyl ammonio) propane sulfonate (DPS) and Brij 30 and homogenized (IKA disperser) on ice for 1 minute to extract the proteins from the skin samples. The homogenate was then centrifuged at 10,000 rpm for 5 minutes and the supernatant was collected. The total protein concentration was determined using the Micro BCA Protein Assay Kit (Pierce). GAPDH levels were measured using the Kdalert™ GAPDH Assay kit (Ambion).

Figure 12:
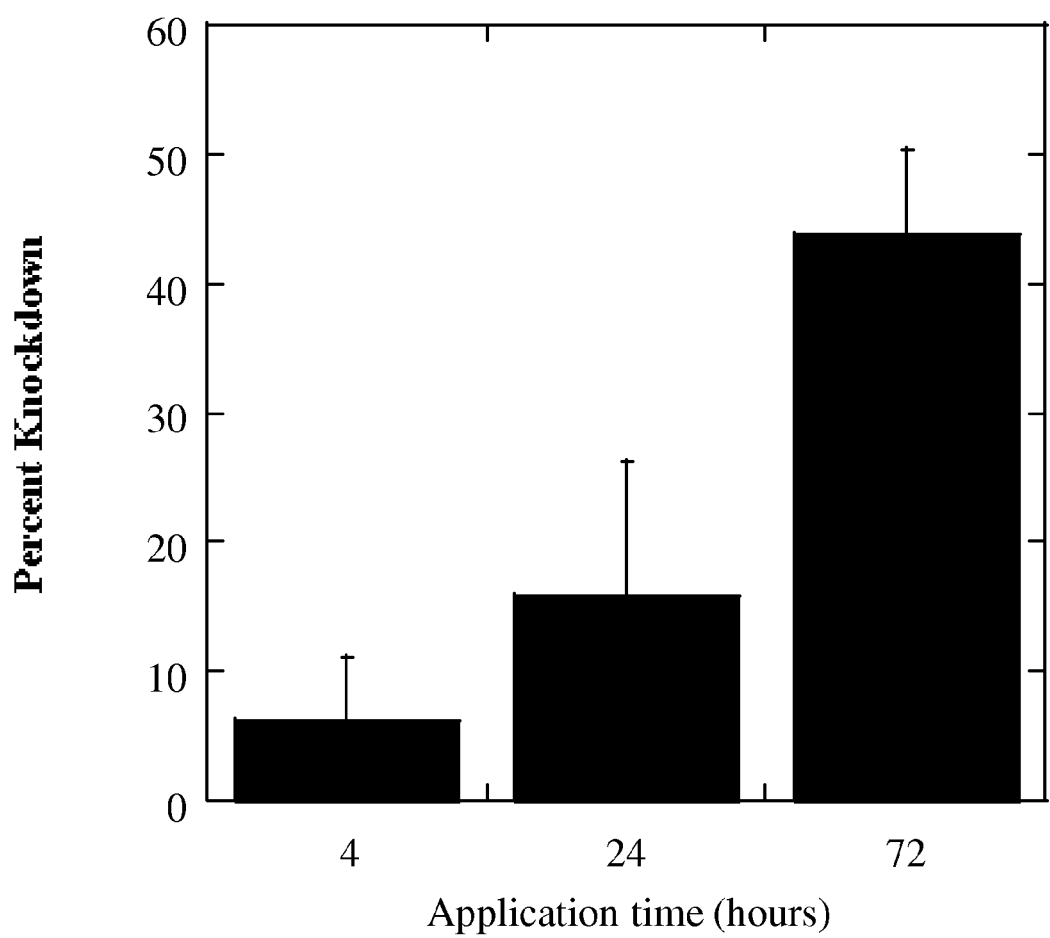
FIG. 12 shows the results for GAPDH knockdown at various application times using peptide-conjugated GAPDH siRNA. The reduction in GAPDH protein levels after SPACE-GAPDH siRNA application times of 4, 24, and 72 hours.

Animals treated with SPACE-GAPDH siRNA conjugate induced significant reduction in protein levels compared to controls (no treatment, siRNA alone, SPACE peptide alone and SPACE-conjugated to control siRNA, FIG. 11, panel (c)). Knockdown of GAPDH in skin was dose dependent; 43% knockdown was observed at 10 µM, 21% knockdown at 5 µM, and 10% knockdown at 1 µM (FIG. 11, panel (d)). Knockdown was also dependent on application time with longer application times resulting in higher knockdown (FIG. 12).

What is claimed is:

1. A composition comprising a peptide comprising the amino acid sequence selected from the group consisting of CHSALTKHC (SEQ ID NO:8), CKTGSHNQC (SEQ ID NO:9), CMGPSSMLC (SEQ ID NO: 10), CTDPNQLQC (SEQ ID NO: 11), CSTHFIDTC (SEQ ID NO: 12), ACTGSTQHQCG (SEQ ID NO: 13), ACHSALTKHCG (SEQ ID NO: 14), ACKTGSHNQCG (SEQ ID NO: 15), ACMGPSSMLCG (SEQ ID NO: 16), ACTDPNQLQCG (SEQ ID NO: 17), and ACSTHFIDTCG (SEQ ID NO: 18), wherein the peptide is associated with or conjugated to an active agent or an active agent carrier comprising the active agent, and wherein the composition is capable of penetrating a stratum corneum (SC) layer when contacted therewith or penetrating a cell when contacted therewith.

2. The composition of claim 1, wherein the composition is capable of penetrating the SC layer and penetrating the cell.

3. The composition of claim 1, wherein the peptide is a cyclic peptide comprising a Cys-Cys disulfide bond.

4. The composition of claim 1, wherein the composition is capable of penetrating the cellular membrane of a cell selected from the group consisting of a viable non-human animal cell, a viable human cell, a viable epidermal cell, a viable dermal cell, and a viable immunological cell.

5. The composition of claim 1, wherein the active agent comprises a protein, a nucleic acid, a pharmaceutical compound, a detectable agent, a nanoparticle, or a low molecular weight compound.

6. The composition of claim 5, wherein the active agent comprises a protein and the protein comprises an antibody or a fragment thereof comprising at least one paratope.

7. The composition of claim 5, wherein the active agent comprises a nucleic acid and the nucleic acid is DNA.

8. The composition of claim 5, wherein the active agent comprises a nucleic acid and the nucleic acid is RNA.

9. The composition of claim 8, wherein the RNA is interfering RNA.

10. The composition of claim 9, wherein the interfering RNA is an shRNA, an miRNA, or an siRNA.

11. The composition of claim 10, wherein the interfering RNA is an siRNA and the siRNA is selected from the group consisting of an IL-10 siRNA, a CD86 siRNA, a KRT6a siRNA, a TNFR1 siRNA, and a TACE siRNA.

12. The composition of claim 10, wherein the interfering RNA is an siRNA and the siRNA is a mutation-specific siRNA.

13. The composition of claim 5, wherein the active agent comprises a detectable agent and the detectable agent comprises a fluorescent label or a radioactive label.

14. The composition of claim 1, wherein the active agent is an inhibitor of IL-10 biological activity.

15. The composition of claim 14, wherein the active agent is selected from an IL-10 siRNA and antibodies or fragments thereof that bind IL-10.

16. The composition of claim 1, wherein the peptide is conjugated to the active agent carrier comprising the active agent and the active agent carrier is selected from the group consisting of a liposome, a nanoparticle, and a polymeric micelle.

17. The composition of claim 1, wherein the peptide is associated with the active agent or the active agent carrier comprising the active agent, via hydrophobic, electrostatic or van der Walls interactions.

18. An isolated peptide comprising the amino acid sequence selected from one of the following sequences: CHSALTKHC (SEQ ID NO:8), CKTGSHNQC (SEQ ID NO:9), CMGPSSMLC (SEQ ID NO: 10), CTDPNQLQC (SEQ ID NO: 11), CSTHFIDTC (SEQ ID NO: 12), ACTGSTQHQCG (SEQ ID NO: 13), ACHSALTKHCG (SEQ ID NO: 14), ACKTGSHNQCG (SEQ ID NO: 15), ACMGPSSMLCG (SEQ ID NO: 16), ACTDPNQLQCG (SEQ ID NO: 17), and ACSTHFIDTCG (SEQ ID NO: 18), wherein the peptide is associated with or conjugated to an active agent or an active agent carrier comprising the active agent, and wherein the composition is capable of penetrating a stratum corneum (SC) layer when contacted therewith or penetrating a cell when contacted therewith.

19. The isolated peptide of claim 18, wherein the peptide comprises repeat units of one or more of CHSALTKHC (SEQ ID NO:8), CKTGSHNQC (SEQ ID NO:9), CMGPSSMLC (SEQ ID NO:10), CTDPNQLQC (SEQ ID NO:11), CSTHFIDTC (SEQ ID NO:12), ACTGSTQHQCG (SEQ ID NO:13), ACHSALTKHCG (SEQ ID NO:14), ACKTGSHNQCG (SEQ ID NO:15), ACMGPSSMLCG (SEQ ID NO:16), ACTDPNQLQCG (SEQ ID NO:17), and ACSTHFIDTCG (SEQ ID NO:18).

20. The isolated peptide of claim 19, wherein the unit is repeated 2 to 50 times.

21. The isolated peptide of claim 19, wherein each unit is separated by an intervening peptide sequence.

22. The isolated peptide of claim 18, wherein the peptide is a cyclic peptide comprising a Cys-Cys disulfide bond.

23. A composition comprising a peptide consisting of the amino acid sequence selected from one of the following sequences: CHSALTKHC (SEQ ID NO:8), CKTGSHNQC (SEQ ID NO:9), CMGPSSMLC (SEQ ID NO: 10), CTDPNQLQC (SEQ ID NO: 11), CSTHFIDTC (SEQ ID NO: 12), ACTGSTQHQCG (SEQ ID NO: 13), ACHSALTKHCG (SEQ ID NO: 14), ACKTGSHNQCG (SEQ ID NO: 15), ACMGPSSMLCG (SEQ ID NO: 16), ACTDPNQLQCG (SEQ ID NO: 17), and ACSTHFIDTCG (SEQ ID NO: 18), wherein the peptide is associated with or conjugated to an active agent or an active agent carrier comprising the active agent, and wherein the composition is capable of penetrating a stratum corneum (SC) layer when contacted therewith or penetrating a cell when contacted therewith.

24. The composition of claim 1, wherein the peptide comprises SEQ ID NO. 13.

25. The composition of claim 1, wherein the peptide comprises SEQ ID NO. 14.

26. The composition of claim 1, wherein the peptide comprises SEQ ID NO. 15.

27. The composition of claim 1, wherein the peptide comprises SEQ ID NO. 16.

28. The composition of claim 1, wherein the peptide comprises SEQ ID NO. 17.

29. The composition of claim 3, wherein the peptide comprises SEQ ID NO. 13.

30. The composition of claim 3, wherein the peptide comprises SEQ ID NO. 14.

31. The composition of claim 3, wherein the peptide comprises SEQ ID NO. 15.

32. The composition of claim 3, wherein the peptide comprises SEQ ID NO. 16.

33. The composition of claim 3, wherein the peptide comprises SEQ ID NO. 17.

34. The isolated peptide of claim 18, wherein the peptide comprises SEQ ID NO. 13.

35. The isolated peptide of claim 18, wherein the peptide comprises SEQ ID NO. 14.

36. The isolated peptide of claim 18, wherein the peptide comprises SEQ ID NO. 15.

37. The isolated peptide of claim 18, wherein the peptide comprises SEQ ID NO. 16.

38. The isolated peptide of claim 18, wherein the peptide comprises SEQ ID NO. 17.

39. The composition of claim 23, wherein the peptide is a cyclic peptide comprising a Cys-Cys disulfide bond.

40. The composition of claim 1, wherein the peptide is from 9 to 11 amino acids in length.

41. The composition of claim 1, wherein the peptide is from about 12-15 amino acids in length.

42. The composition of claim 1, wherein the peptide is from about 16-19 amino acids in length.

* * * * *

UNITED STATES PATENT AND TRADEMARK OFFICE
CERTIFICATE OF CORRECTION

PATENT NO. : 8,518,871 B2  
APPLICATION NO. : 13/253796  
DATED : August 27, 2013  
INVENTOR(S) : Tracy Hsu et al.

Page 1 of 1

It is certified that error appears in the above-identified patent and that said Letters Patent is hereby corrected as shown below:

In the Specification

Column 1, line 22,

Please replace "This invention was made with Government support under Federal Grant No. 1UO1 HL080718 awarded by the National Institutes of Health and Federal Grant No. 1S10RR017753-01 awarded by the National Center for Research Resources. The Government has certain rights in this invention" with --This invention was made with Government support under Grant Nos. S10 RR017753-01 and U01 HL080718, awarded by the National Institutes of Health. The Government has certain rights in this invention.--

Signed and Sealed this  
Fourth Day of November, 2014

Michelle K. Lee  
*Deputy Director of the United States Patent and Trademark Office*